(12) United States Patent
Craig et al.

(10) Patent No.: US 10,679,728 B2
(45) Date of Patent: Jun. 9, 2020

(54) METHOD OF CHARACTERIZING SEQUENCES FROM GENETIC MATERIAL SAMPLES

(71) Applicants: THE TRANSLATIONAL GENOMICS RESEARCH INSTITUTE, Phoenix, AZ (US); The Regents of the University of California, Oakland, CA (US)

(72) Inventors: David Craig, Chandler, AZ (US); Nils Homer, Los Angeles, CA (US)

(73) Assignees: The Translational Genomics Research Institute, Phoenix, AZ (US); The Regents of the University of California, Oakland, CA (US)

( * ) Notice: Subject to any disclaimer, the term of this patent is extended or adjusted under 35 U.S.C. 154(b) by 303 days.

(21) Appl. No.: 15/477,808

(22) Filed: Apr. 3, 2017

(65) Prior Publication Data

US 2017/0206311 A1    Jul. 20, 2017

Related U.S. Application Data

(63) Continuation of application No. 12/507,695, filed on Jul. 22, 2009, now abandoned.

(60) Provisional application No. 61/082,912, filed on Jul. 23, 2008.

(51) Int. Cl.
| | |
|---|---|
| *G01N 33/48* | (2006.01) |
| *G16B 20/00* | (2019.01) |
| *G16B 25/00* | (2019.01) |
| *G16B 40/00* | (2019.01) |
| *G06G 7/58* | (2006.01) |

(52) U.S. Cl.
CPC ............. *G16B 20/00* (2019.02); *G16B 25/00* (2019.02); *G16B 40/00* (2019.02)

(58) Field of Classification Search
None
See application file for complete search history.

*Primary Examiner* — Eric S Dejong
(74) *Attorney, Agent, or Firm* — Rodney J. Fuller; Booth Udall Fuller, PLC

(57) ABSTRACT

Among other aspects provided herein is a method describing the use of Single Nucleotide Polymorphism (SNP) genotyping microarrays to resolve whether genetic material (such as genomic DNA) derived from a particular individual is present in a genetic material mixture (such as a complex genomic DNA mixture) is disclosed. Furthermore, it is demonstrated that the identification of the presence of genetic material (such as genomic DNA) of specific individuals within a series of complex genomic mixtures is possible.

25 Claims, 9 Drawing Sheets

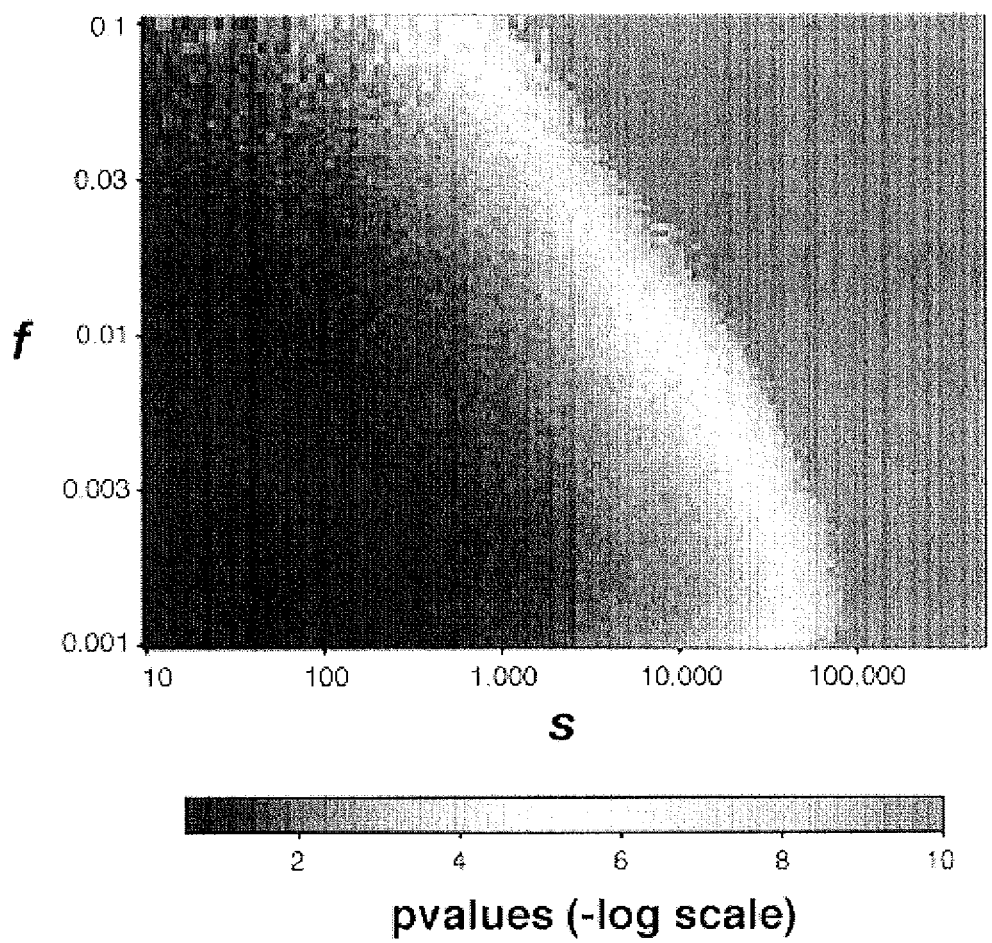
Figure 2a - $s$ vs. $f$ ($v_p=0.001$)

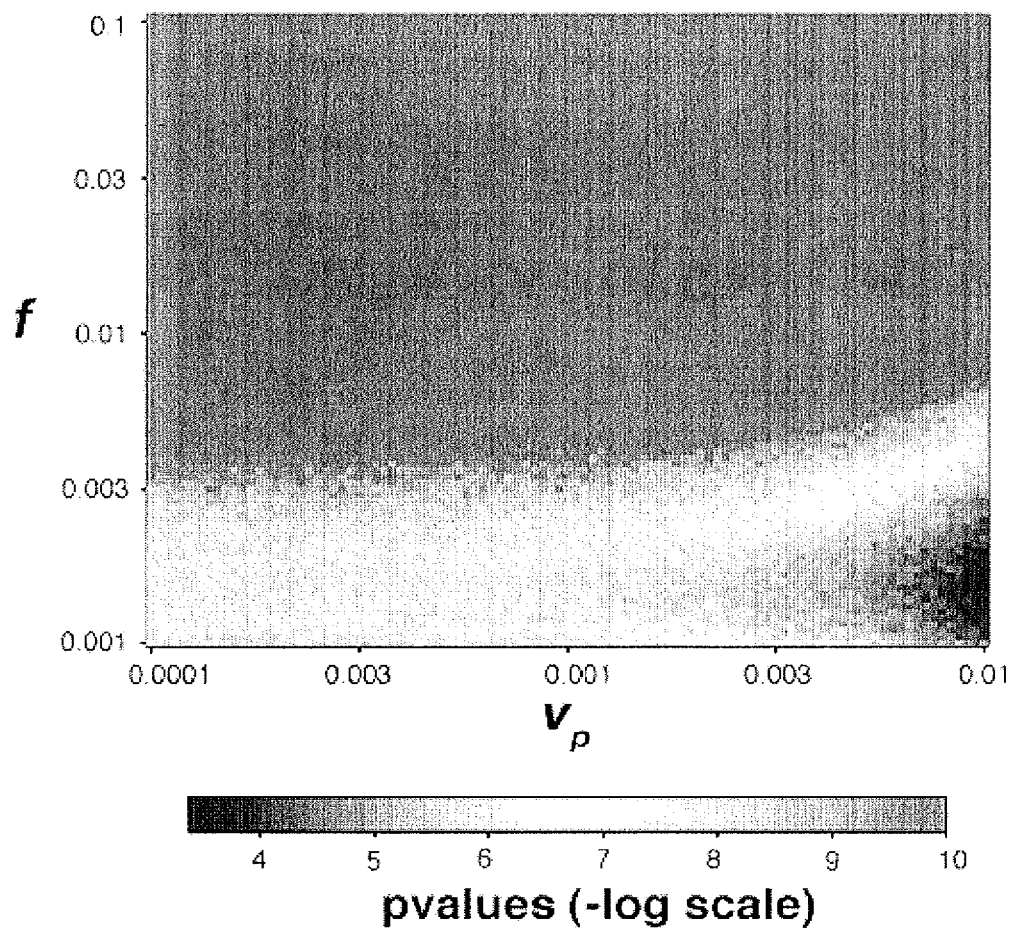
Figure 2b - $v_p$ vs. $f$ ($s=50,000$)

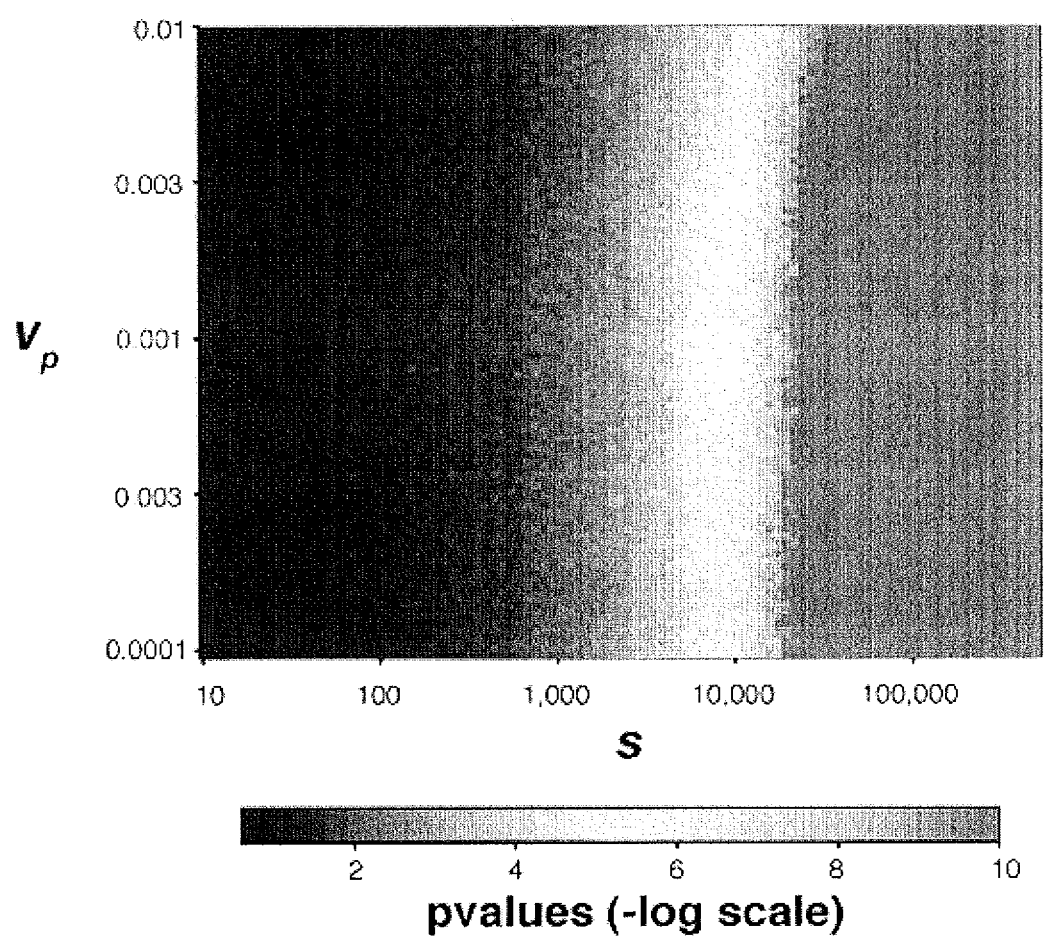
Figure 2c - $s$ vs. $v_p$ ($f=0.01$)

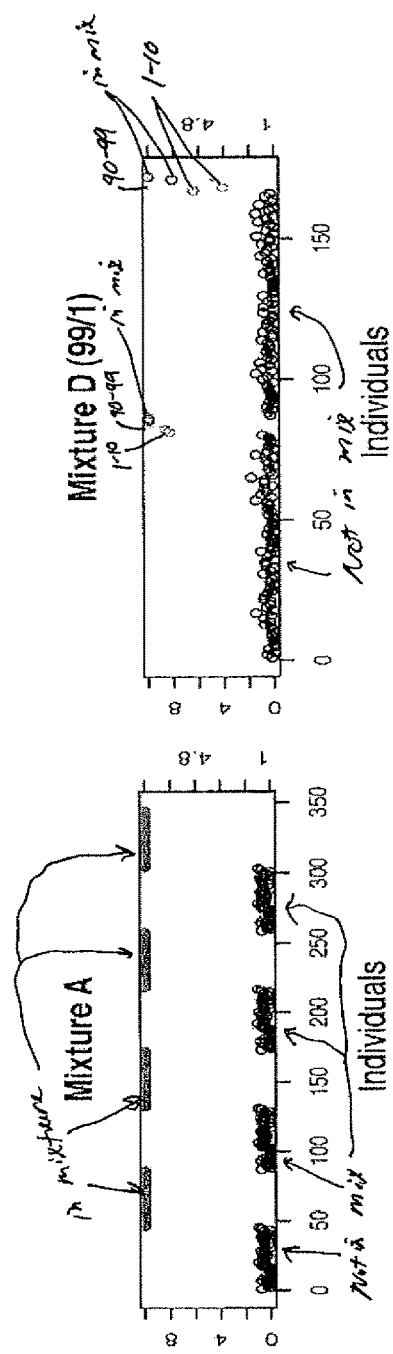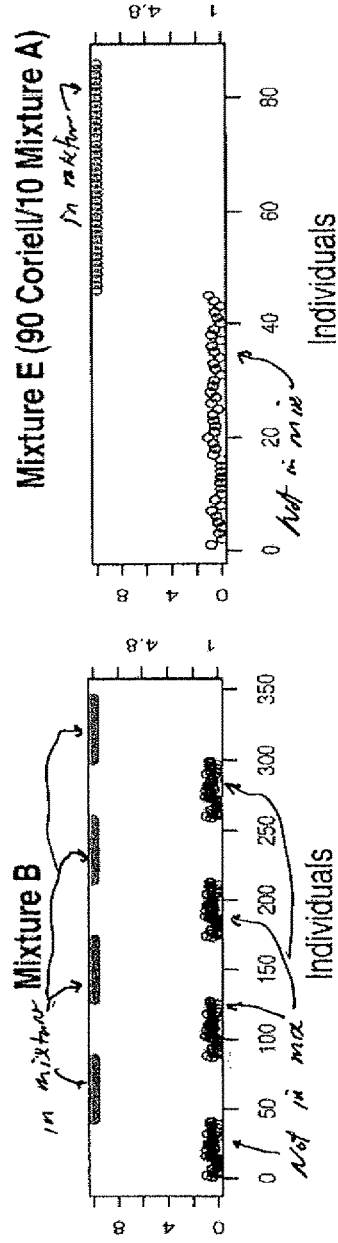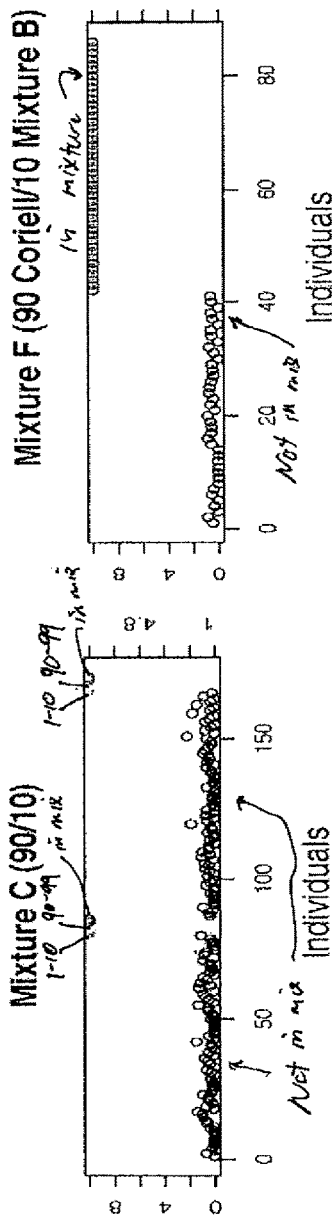
FIG. 3A
Illumina 550K all SNPs

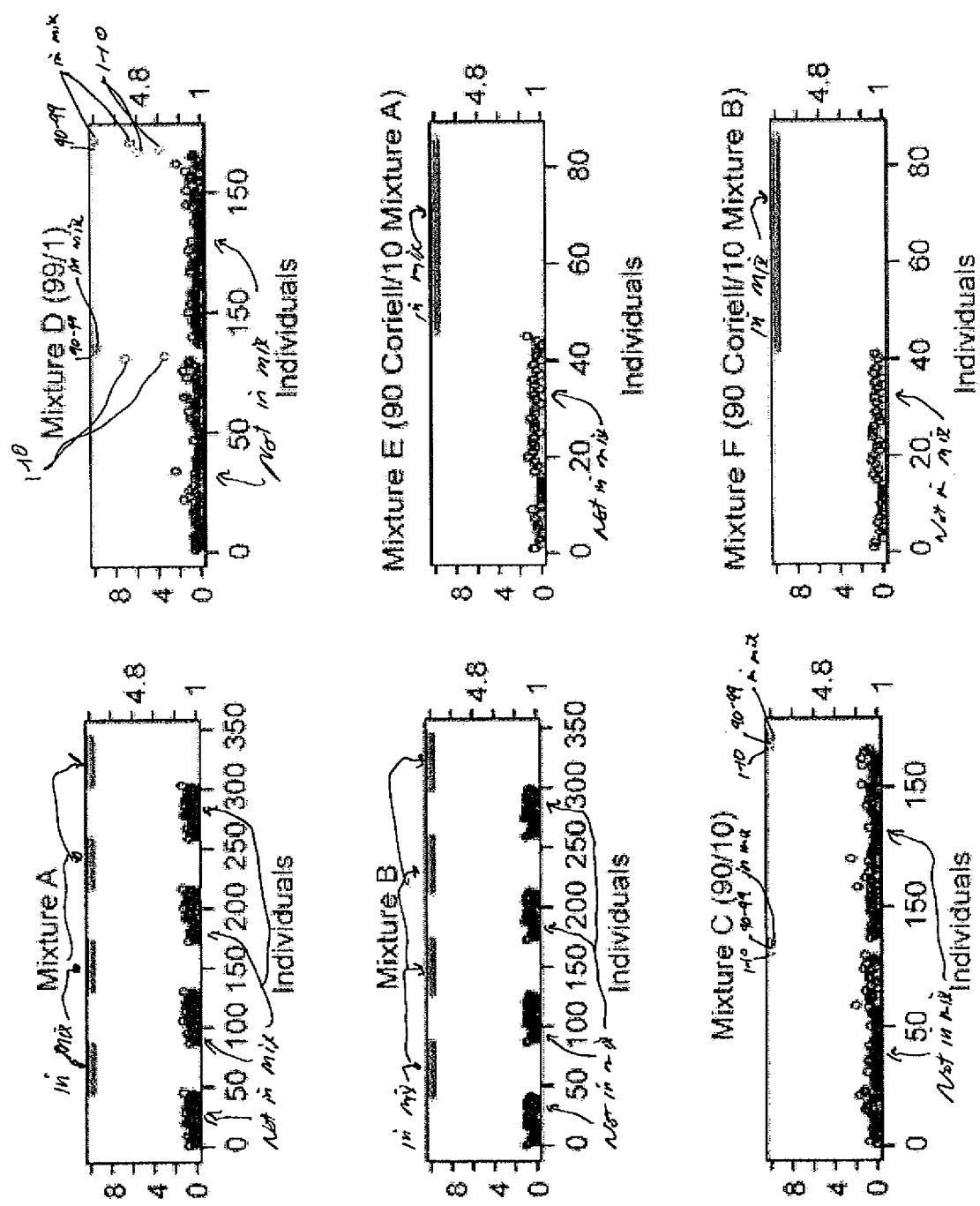

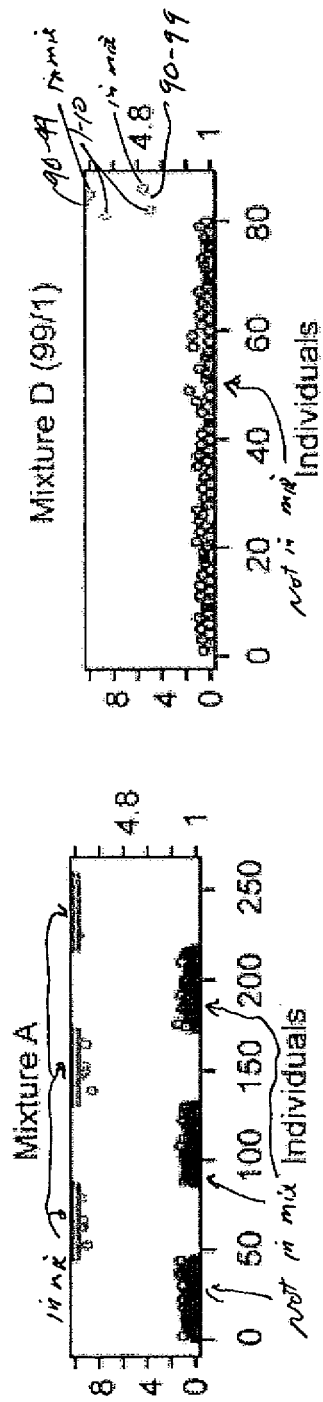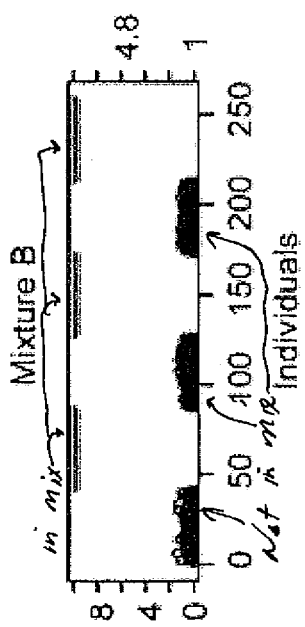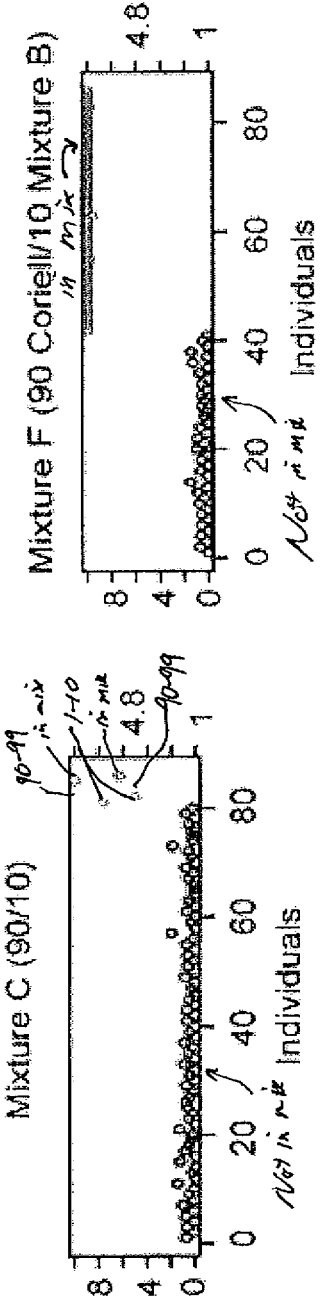
FIG. 3C
Affymetrix all SNPs

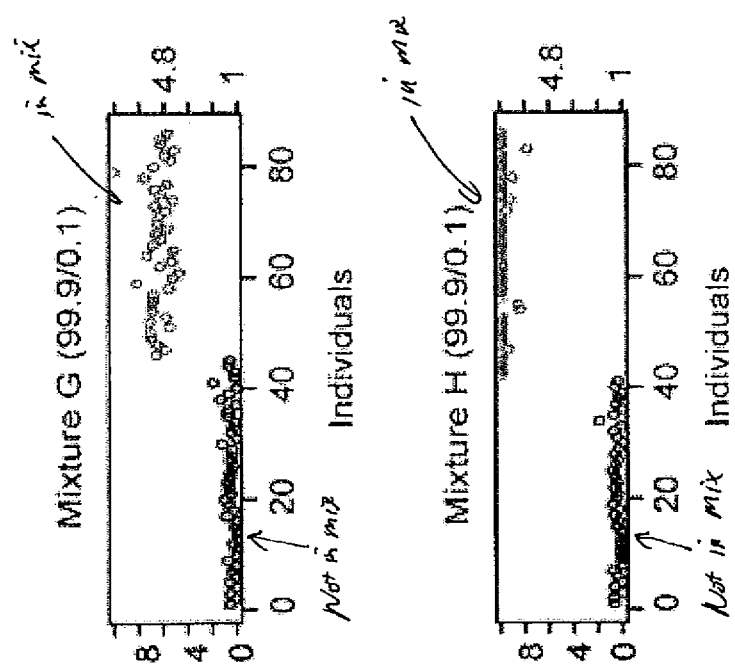

METHOD OF CHARACTERIZING SEQUENCES FROM GENETIC MATERIAL SAMPLES

CROSS-REFERENCE TO RELATED APPLICATIONS

The present application is a continuation of U.S. patent application Ser. No. 12/507,695, filed Jul. 22, 2009 (published as US 20100086926), which claims priority to U.S. Provisional Application No. 61/082,912, filed Jul. 23, 2008, the contents of each of which are hereby incorporated by reference in their entireties.

STATEMENT REGARDING FEDERALLY SPONSORED R&D

The US government retains certain rights in this invention as provided by the terms of grant number 5U01HL086528 awarded by the National Institutes of Health.

COPYRIGHT NOTICE

A portion of the disclosure of this patent document contains material which is subject to (copyright or mask work) protection. The (copyright or mask work) owner has no objection to the facsimile reproduction by anyone of the patent document or the patent disclosure, as it appears in the Patent and Trademark Office patent file or records, but otherwise reserves all (copyright or mask work) rights whatsoever.

INCORPORATION BY REFERENCE

The present application is being filed along with a computer program listing appendix in electronic format. The computer program listing appendix is provided as a file entitled Program_TGEN-001A.txt, created on Jul. 20, 2009, which is 138,764 bytes in size. The information in the electronic format of the computer program listing appendix is incorporated herein by reference in its entirety. FIELD OF THE INVENTION The present disclosure relates to systems and methods for using multiple single nucleotide polymorphisms (SNPs) for characterizing genetic material in a sample. BACKGROUND OF THE INVENTION Resolving whether an individual's genetic material is present within a complex mixture containing genetic material (such as DNA) from numerous individuals is of interest to multiple fields. For example, within forensics, determining whether a person contributed their genetic material to a mixture is typically a skilled process. In large part, forensically identifying whether a person is contributing less than 10% of the total genomic DNA to a mixture is not easily done, is difficult to automate, and is highly confounded with the inclusion of more individuals.

Numerous methods examining DNA mixtures currently exist, most of these addressing mixtures with smaller numbers of individuals within forensics studies (See Egeland, T., Dalen, I. & Mostad, P. F. Estimating the number of contributors to a DNA profile. *Int J Legal Med* 117, 271-275 (2003); Hu, Y. Q. & Fung, W. K. Interpreting DNA mixtures with the presence of relatives. *Int J Legal Med* 117, 39-45 (2003); and Balding, D. J. Likelihood-based inference for genetic correlation coefficients. *Theor Popul Biol* 63, 221-230 (2003)). Using short tandem repeats (STR) is a common method to generate DNA genotyping profiles and allows for identification of the various alleles and their relative quantity within the mixture (See Clayton, T. M., Whitaker, J. P., Sparkes, R. & Gill, P. Analysis and interpretation of mixed forensic stains using DNA STR profiling. *Forensic Sci Int* 91, 55-70 (1998); Cowell, R. G., Lauritzen, S. L. & Mortera, J. Identification and separation of DNA mixtures using peak area information. *Forensic Sci Int* 166, 28-34 (2007); Pearson, J. V. et al. Identification of the genetic basis for complex disorders by use of pooling-based genomewide single-nucleotide-polymorphism association studies. *Am J Hum Genet* 80, 126-139 (2007); and Bill, M. et al. PENDULUM—a guideline-based approach to the interpretation of STR mixtures. *Forensic Sci Int* 148, 181-189 (2005)). Frequently, STRs on the Y chromosome are useful when resolving the male components of the mixture (See Jobling, M. A. & Gill, P. Encoded evidence: DNA in forensic analysis. *Nat Rev Genet* 5, 739-751 (2004)). Nevertheless, these methods based on STRs expectedly suffer from limited power when using severely degraded DNA (See Jobling, M. A. & Gill, P. Encoded evidence: DNA in forensic analysis. *Nat Rev Genet* 5, 739-751 (2004); and Ladd, C., Lee, H. C., Yang, N. & Bieber, F. R. Interpretation of complex forensic DNA mixtures. *Croat Med J* 42, 244-246 (2001)). Mitochondrial DNA (mtDNA) based on hypervariable region sequencing is useful when analyzing degraded DNA due to its high copy number and improved stability. Profiles derived from mtDNA can also be combined with STR analysis to acheive better identification (See Goodwin, W., Linacre, A. & Vanezis, P. The use of mitochondrial DNA and short tandem repeat typing in the identification of air crash victims. *Electrophoresis* 20, 1707-1711 (1999)). Nonetheless, mtDNA has weaknesses, including the uniparental mode of inheritance and lower discrimination power that can be moderately mediated by using the whole mitochondrial genome or known surrounding single nucleotide polymorphisms (SNPs) (See Coble, M. D. et al. Single nucleotide polymorphisms over the entire mtDNA genome that increase the power of forensic testing in Caucasians. *Int J Legal Med* 118, 137-146 (2004) and Parsons, T. J. & Coble, M. D. Increasing the forensic discrimination of mitochondrial DNA testing through analysis of the entire mitochondrial DNA genome. *Croat Med J* 42, 304-309 (2001)). Informative SNPs have been used to help resolve problems with using mtDNA (See Coble, M. D. et al. Single nucleotide polymorphisms over the entire mtDNA genome that increase the power of forensic testing in Caucasians. *Int J Legal Med* 118, 137-146 (2004); Just, R. S. et al. Toward increased utility of mtDNA in forensic identifications. *Forensic Sci Int* 146 Suppl, S147-149 (2004); and Vallone, P. M., Just, R. S., Coble, M. D., Butler, J. M. & Parsons, T. J. A multiplex allele-specific primer extension assay for forensically informative SNPs distributed throughout the mitochondrial genome. *Int J Legal Med* 118, 147-157 (2004)) but have not been used wholly or separately as the discriminatory factor, or on the same scale as provided herein.

Aspects and applications of the invention presented here are described below in the drawings and detailed description of the invention.

SUMMARY OF THE INVENTION

Some of the present embodiments provide a variety of methods (and apparatuses for implementing these methods), for determining if a subject's genetic material is present in a genetic material sample (a "test genetic material sample). While there are a variety of techniques by which this can be achieved, in some embodiments, this is achieved by determining if there is a bias and/or direction of an allele occurrence and/or frequency within a collection of single nucleotide polymorphisms (SNPs) of the test genetic material sample relative to a reference and/or the subject's SNP signature or collection of SNPs genotypes.

In some embodiments, a system for determining if a subject contributed genetic material to a sample is provided. The system can comprise an input module configured to allow the input of one or more of a sample SNP signature, a reference SNP signature, and a subject SNP signature; a module configured to determine a bias of an allele frequency within SNPs of the sample SNP signature relative to the reference SNP signature and the subject SNP signature; and a module configured to output the bias, wherein one or more of the modules is executed on a computing device.

In some embodiments, a method for determining if a person of interest contributed genetic material to a test genetic material sample is provided. The method can comprise determining a bias of an allele frequency within SNPs of the test genetic material sample relative to a reference and a subject's SNP signature.

In some embodiments, a method of characterizing a test genetic material sample to determine if a person of interest's ("POI's") genetic material is within the test genetic material sample is provided. The method can comprise providing a SNP analysis of the test genetic material sample; providing a SNP analysis of a reference genetic material sample; providing a SNP analysis of a POI's genetic material; in a first comparison, comparing the SNP analysis of the test genetic material sample to the SNP analysis of the POI's genetic material; in a second comparison, comparing the SNP analysis of the reference genetic material to the SNP analysis of the POI's genetic material; and comparing the first and second comparisons, thereby determining if the POI's genetic material is likely in the test genetic material sample.

In some embodiments, a method of characterizing a test genetic material sample is provided. The method can comprise providing a first allele frequency for a SNP for a person of interest (POI); providing a second allele frequency for the SNP from a reference population(s) of genetic material; providing a third allele frequency for the SNP for the test genetic material sample; repeating the above processes for at least 10 different SNPs; and analyzing the first, second, and third allele frequencies to characterize the test genetic material sample.

In some embodiments, a method for determining a likelihood that a subject contributed genetic material to a test genetic material sample is provided. The method can comprise providing a test genetic material sample; performing a single nucleotide polymorphism analysis on the test genetic material sample, whereby at least 50 different single nucleotide polymorphisms in said test genetic material sample are analyzed, thereby creating a sample SNP signature; and comparing the sample SNP signature to a subject's SNP signature to determine a likelihood that the subject contributed genetic material to a test genetic material sample.

Previously, within the field of forensics, as well as the field of human genetics, there was a base assumption that it was not possible to identify individuals using pooled data (e.g. allele frequency) from SNP data. Some of the embodiments provided herein provide methods of using hundreds or thousands of SNPs (optionally assayed on a high-density microarray) to resolve trace contributions of DNA (or other genetic material) to a complex mixture. In some embodiments, this can specifically exploit raw allele intensity measures in the analysis of DNA with mixed samples and a genotype calling algorithm to digitize the inherently analog information derived from an SNP assay (See, e.g., Kennedy, G. C. et al. Large-scale genotyping of complex DNA. *Nat Biotechnol* 21, 1233-1237 (2003)).

In some embodiments, the invention relates generally to single nucleotide polymorphism genotyping and more specifically to single nucleotide polymorphism genotyping of samples from multiple individuals and/or sources.

In some embodiments, the method comprises a sample SNP signature that is from a biopsy from a subject, wherein the biopsy from the subject is to be tested for the presence of a cancer. In some embodiments, the sample SNP signature is created from a female who wants to determine if she is pregnant. In some embodiments, the subject's SNP signature is a viral DNA signature.

BRIEF DESCRIPTION OF THE SEVERAL VIEWS OF THE DRAWINGS

A more complete understanding of various embodiments of the present inventions can be derived by referring to the detailed description when considered in connection with the following illustrative figures. In the figures, like reference numbers refer to like elements or acts throughout the figures.

FIGS. 2A-2C depict various simulation results: Using 1423 Wellcome Trust 58C individuals, log scaled p-values were given from simulations based off of three variables: the number of SNPs (s), the fraction of the individual in the mixture (f), and the probe variance ($v_p$). The graphs plot the relationships between the three variables with a different variable fixed in each graph. The log scaled p-values are represented by the shading of each point in the graph, as well as the z-axis on the right graphs. These simulations indicate that one can resolve mixtures where a given individual is 0.1% of the mixture (f), probe variance is at most 0.01 ($v_p$) and the number of SNPs probed is 50,000 (s).

FIGS. 3A-3D provide the results from a series of experiments. Experimental validation using a series of mixtures (see Table 1, A-F) assayed on the Affymetrix GeneChip 5.0, Illumina BeadArray 550 and the Illumina 450S Duo Human BeadChip. The x-axis shows each individual in the CEU HapMap population, the left y-axis shows the p-value (log scaled), and the right y-axis shows the value of the test statistic. With regard to mixtures A, B, E and F those in the mixture are shaded light and identified and those not in the mixture are shaded darker and identified. With regard to mixtures C and D those individuals who are not in the mixtures are shaded darkly and identified, those individuals who are related to the 1% or 10% individuals in the mixtures are shaded lighter and identified as "1-10", those individuals who are related to the 90% or 99% are shaded lighter still and identified as "90-99", and those people in the mixture are shaded lighter than those absent from the mixture and are identified. In all mixtures, the identification of the presence of a person's genomic DNA was possible. An arrow denotes identification of numerous (or a cluster) of data points while a line denotes identification of a specific data point. Unless otherwise specified, an unmarked data point is part of the closest denoted cluster.

Figure 1A:
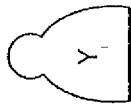
FIG. 1A. To give insight into the intuition behind come embodiments of the various methods, three different scenarios are presented per SNP of the possible allele frequency of the person of interest corresponding to the genotypes AA, AB, and BB. The allele frequencies of the reference population, person of interest (subject), and the mixture are described as $M_i$ (test genetic material sample), $Y_i$ (subject), and $Pop_i$ (reference population) respectively. The distance measure is greater (and positive) when the $Y_i$ of the person of interest is closer to the $M_i$ of the mixture than to the $Pop_i$ of the reference population. Similarly, the distance measure is smaller (and negative) when the $Y_i$ of the person of interest is closer to the $Pop_i$ of the reference population than to $M_i$ of the mixture. the test statistic is then the z-score using this distance measure.

Elements and acts in the figures are illustrated for simplicity and have not necessarily been rendered according to any particular sequence or embodiment.

DETAILED DESCRIPTION OF THE INVENTION

In the following description, and for the purposes of explanation, numerous specific details are set forth in order to provide a thorough understanding of the various aspects of the invention. It will be understood, however, by those skilled in the relevant arts, that the present embodiments can be practiced without these specific details. In other instances, known structures and devices are shown or discussed more generally in order to avoid obscuring the invention. In many cases, a description of the operation is sufficient to enable one to implement the various forms of the invention, particularly when the operation is to be implemented in software. It should be noted that there are many different and alternative configurations, devices and technologies to which the disclosed inventions may be applied. The full scope of the various embodiments and the inventions themselves are not limited to the examples that are described below.

The present disclosure provides a variety of methods (and apparatuses for implementing these methods), for determining if a subject's genetic material is present in a genetic material sample (a "test genetic material sample). While there are a variety of techniques by which this can be achieved, in some embodiments, this is achieved by determining if there is a bias and/or direction of an allele occurrence and/or frequency within SNPs of the test genetic material sample relative to a reference and/or the subject's SNP signature (e.g., SNP genotype). Among other aspects provided herein is a method describing the use of Single Nucleotide Polymorphism (SNP) genotyping microarrays to resolve whether genetic material (such as genomic DNA) derived from a particular individual is present in a genetic material mixture (such as a complex genomic DNA mixture). Furthermore, the results presented herein demonstrate that the identification of the presence of genetic material (such as genomic DNA) of specific individuals within a series of highly complex genomic mixtures, including mixtures where an individual contributes less than 0.1% of the total genetic material (such as genomic DNA) is possible. These findings shift the perceived utility of SNPs in the identification of individual trace contributors within a forensics mixture and demonstrates the viability of previously sub-optimal DNA sources due to sample contamination. These findings also indicate that composite statistics across cohorts, such as allele frequency or genotype counts, do not mask identity within genome-wide association studies.

While SNPs and high-density SNP genotyping arrays have been around for some time, their use has been predominately been developed as tools geneticists use to identify common genetic variants that predispose an individual to disease. Some embodiments disclosed herein allow for the use of SNPs to identify the presence or absence of one or more individuals' genetic material in a sample.

In some embodiments, the SNP based analysis can be used for analyzing forensic mixtures. SNPs are traditionally analyzed by genotype (e.g. AA, AT, or TT) and, prior to the present disclosure, were thought to be non-ideal in resolving mixtures. It has been argued that their poor performance in the analysis of mixed DNA samples is one of the primary reasons SNP genotyping arrays have not become adopted by the forensics community (See Jobling, M. A. & Gill, P. Encoded evidence: DNA in forensic analysis. *Nat Rev Genet* 5, 739-751 (2004) and Kidd, K. K. et al. Developing a SNP panel for forensic identification of individuals. *Forensic Sci Int* 164, 20-32 (2006)). Other methods have employed match probability estimation after inferring genotypes using STRs where the probability of two unrelated individuals sharing a combination of markers is assessed (See Jobling, M. A. & Gill, P. Encoded evidence: DNA in forensic analysis. *Nat Rev Genet* 5, 739-751 (2004)). Exclusion probabilities give a calculation based on the probability of excluding a random individual (See Chakraborty, R., Meagher, T. R. & Smouse, P. E. Parentage analysis with genetic markers in natural populations. I. The expected proportion of offspring with unambiguous paternity. *Genetics* 118, 527-536 (1988)). Nevertheless, many of these methods rely on assuming the number of individuals in the mixture (See Egeland, T., Dalen, I. & Mostad, P. F. Estimating the number of contributors to a DNA profile. *Int J Legal Med* 117, 271-275 (2003)) and have been applied only to STR markers. In some embodiments, one need not know or estimate the number of individuals that contributed to a mixture when using the methods disclosed herein.

Likelihood ratios are commonly used when testing which hypothesis is favored by the evidence or DNA samples (See Weir, B. S. et al. Interpreting DNA mixtures. *J Forensic Sci* 42, 213-222 (1997)). In some embodiments, one can compute the likelihood ratio of two hypotheses: the individual contributes to the mixture and the individual does not contribute to the mixture. In some embodiments, the proper prior odds ratio can then be given based on the current situation or context, and then would be combined with the likelihood ratio to give a posterior odd ratio. In some embodiments, one can then use SNP microarrays to determine allele frequencies or allele counts. This is especially advantageous since training datasets such as from the HapMap Project or 1000 Genomes project are readily available and could be used to calculate the probability of the observed mixture's allele frequency or individual of interest's genotype. In some embodiments, the Bayesian approach includes creation of explicit hypotheses, estimation of the total fraction of the individual of interest that contributes to the mixture, inclusion of multiple ancestral backgrounds across ancestrally informative SNPs, and inclusion of the possibility that related individuals are within the mixture.

The present disclosure presents a detailed description of some of various embodiments noted above, as well as additional embodiments. The following section briefly outlines some of the various terms, and is followed by a more detailed description of some of the proof of principle and exemplary embodiments for some of the techniques. Following this section is a selection of various additional embodiments for the various components and/or parts of some of the embodiments, which is followed by a set of examples for some of the various embodiments.

Definitions

The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the invention. The term "and/or" denotes that the provided possibilities can be used together or be used in the alternative. Thus, the term "and/or" denotes that both options exist for that set of possibilities.

Unless otherwise defined, scientific and technical terms used in connection with the invention described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used, for example, for genetic material (nucleic acid) purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. 2000). The nomenclatures utilized in connection with, and the laboratory procedures and techniques of described herein are those well known and commonly used in the art.

The inventors are fully aware that they can be their own lexicographers if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain and ordinary meaning to the terms be applied to the interpretation of the specification and claims.

As utilized in accordance with the embodiments provided herein, the following terms, unless otherwise indicated, shall be understood to have the following meanings:

The term "genetic material" refers to natural nucleic acids, artificial nucleic acids, non-natural nucleic acid, orthogonal nucleotides, analogs thereof, or combinations thereof. Genetic material can also include analogs of DNA or RNA having modifications to either the bases or the backbone. For example, genetic material, as used herein, includes the use of peptide nucleic acids (PNA). The term "genetic material" also includes chimeric molecules. The genetic material can include, consist, or consist essentially of a nucleic acid of one or more strands of single and/or double stranded material. Genetic material from a subject is generally (unless noted otherwise) numerous strands and numerous genes, and in some embodiments, can include the entire genome of the subject. In some embodiments, genetic material comprises, consists or consists essentially of nucleic acids.

In some embodiments, the genetic material is from a subject that someone wishes to determine the presence or absence of in a test genetic material sample. Exemplary genetic materials include DNA, RNA, mRNA, and miRNA. In some embodiments, the genetic material and/or the test genetic material sample comprises, consists, or consists essentially of DNA, RNA, mRNA, miRNA, and any combination thereof. In some embodiments, the genetic material is contained within the test genetic material sample. In other embodiments, the genetic material is not contained within the test genetic material sample. The genetic material can be one or more strands. In some embodiments, the target genetic material comprises a representative selection of nucleic acids. In some embodiments, the target genetic material comprises a genome wide selection of nucleic acids. Unless explicitly noted otherwise, the term "genetic material" can be singular and/or plural (that is, "genetic material" can, for example, denote genetic material from one or more sources).

As used herein, the terms "polynucleotide," "oligonucleotide," and "nucleic acid oligomers" are used interchangeably and mean single-stranded and double-stranded polymers of nucleic acids, including, but not limited to, 2'-deoxyribonucleotides (nucleic acid) and ribonucleotides (RNA) linked by internucleotide phosphodiester bond linkages, e.g. 3'-5' and 2'-5', inverted linkages, e.g. 3'-3' and 5'-5', branched structures, or analog nucleic acids. Polynucleotides have associated counter ions, such as $H^+$, $NH_4^+$, trialkylammonium, $Mg^{2+}$, $Na^+$ and the like. A polynucleotide can be composed entirely of deoxyribonucleotides, entirely of ribonucleotides, or chimeric mixtures thereof. Polynucleotides can be comprised of nucleobase and sugar analogs. Polynucleotides typically range in size from a few monomeric units, e.g. 5-40 when they are more commonly frequently referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytidine, "G" denotes deoxyguanosine, and "T" denotes thymidine.

The term "reduce" denotes some decrease in amount. In some embodiments, an event is reduced by 1, 2, 3, 4, 5, 10, 15, 20, 25, 30, 35, 40, 45, 50, 55, 60, 65, 70, 75, 80, 85, 90, 95, 96, 97, 98, 99, 99.9, 99.99, 99.999, percent or more, including any value above any of the preceding values, as well as any range defined between any two of the preceding values.

For the present application, the term "whole genome" means "genome wide" rather than requiring that the entire genome of any organism be present. Genome wide indicates that there is a sufficient variety and selection of various nucleic acids throughout an organism's genome for the technique being performed. The genome wide selection can be random, throughout an organism's genome, or biased to specific areas. In some embodiments, the genome wide selection is biased to those areas with the specific SNPs to be investigated. In some embodiments it is possible that less than one copy of an entire genome is used, such as in a degraded sample or a haploid sperm cell, as long as sufficient portions of genomic nucleic acid exist at enough SNPs to discriminate between a mixture and a person. This can be as few as a 1,000 SNPs, noting that millions of SNPs are known within the human genome. For example, one can identify an individual using only SNPs on chromosome 1.

The term "test genetic material sample" denotes the sample whose composition is in question. Typically, one would like to know if a specific individual contributed to the genetic material in the test genetic material sample, and/or if other people or organisms contributed to the genetic material in the test genetic material sample. In some embodiments, the test genetic material sample is the sample that is to be or has been assayed for the presence or absence of various SNPs. In some embodiments, the target nucleic acid is contained within the test genetic material sample. In some embodiments, the target nucleic acid is not within the test genetic material sample. The "sample SNP signature" is the SNP signature for the test genetic material sample.

The term "SNP signature" denotes one or more various SNPs and the genotype, alleles, and/or percentage thereof for a collection of SNPs to be assessed. A "reference signature" denotes the alleles present for the SNPs in the reference (or a population thereof). A "test genetic material sample signature" denotes the alleles present for the SNPs in the test genetic material sample. A "subject's SNP signature," "Person of Interest's SNP Signature," or other similar term denotes the alleles present for the SNPs in the subject or Person of Interest. The term SNP signature does not require that the entire SNP signature be used (unless the term "entire" is explicitly used). Thus, comparing, employing and/or using one SNP signature with or to another SNP signature can be achieved merely by comparing a subset of the frequencies of the various alleles or by other approaches described herein. In addition, while a SNP signature can denote one or more various SNP alleles and their frequency (ies), it should be understood that a comparison of the SNP signatures encompasses any comparison of one or more SNPs from one source to one or more alleles from a second source, as such, "comparing" a first and a second SNP signature does not actually require comparing the frequency statistics for each SNP allele (unless explicitly stated), but can be achieved by comparing and/or analyzing any data or computation that relates to these frequencies. As such, the comparison can also be achieved by comparing values (including raw data) that are used to derive the noted frequencies. It can also be achieved by comparing values that are subsequently derived from the noted frequencies. One of skill in the art will appreciate how to maintain the appropriate relationships between the various SNP signatures, based upon the present disclosure.

While the term "person of interest" is occasionally used herein, one of skill in the art will appreciate that the term is generally interchangeable with the term "subject". Thus, in regard to the present disclosure, a "person of interest" is not limited to a human being and, unless specified, can be any subject, such as any subject that includes genetic material (human, mammal, bacterial, viral, etc.). The term "Person of Interest" does denote that the subject is the one whose genetic material is being examined in the test genetic material sample. While this subject can typically be human, for example in many forensics tests, it is not limited to humans, unless explicitly noted.

The term "reference population" denotes a population of one of more reference subjects. The SNP signature of the reference subjects allows for a comparison between the SNP signature of the person of interest and the SNP signature of the test genetic material. A reference population or SNP signature of a reference population is not required for all embodiments disclosed herein. In some embodiments, the reference population and reference SNP signature will have a similar ancestral make-up as that of the sample SNP signature. The term "similar ancestral make-up" can be defined as a genetic distance between individuals or within a population using a set of SNPs or other genetic variants. Thus it is possible for some SNPs to be reserved for assessing ancestry and some SNPs reserved for assign wither a POI is within a mixture. In some embodiments, the reference population should generally match the mixture at the SNPs being interrogated at the SNPs being investigated.

A SNP is an inherited substitution of a nucleotide (for example from A to T, A to G, or G to C) found within more than two individuals. Generally most SNPs exceed a frequency greater than 0.1%, though lower frequency genetic variants are also envisioned. The methods described herein are extendable to other types of genetic variants, including indels, copy number changes, and/or other structural variants.

General Embodiments

Establishment of Test-Statistic.

There are multiple approaches to derive a test-statistic to evaluate a hypotheses that a subject's genetic material is within a mixture, and these are discussed further in herein. In some of the examples below, a frequentist approach is used. In some of the examples below a Bayesian approach, is used. Either can be used depending on the objective of the assay. In some embodiments, other approaches are used without deviating from the present methods.

An overview of some embodiments of the approach is provided in FIG. 1A. In some embodiments, this method can be summarized as the cumulative sum of allele shifts over all available SNPs, where the shift's sign is defined by whether the individual of interest is closer to a reference sample or closer to the given mixture. One aspect of the invention encompasses genotyping a given SNP of a single person, which addresses the original design of SNP genotyping microarrays. In some embodiments, the invention can be further adapted method to mixtures and pooled data.

Genotyping microarray technology can assay millions of SNPs. Genotypes are expected to result from an assay and data is categorical in nature, e.g. AA, AB, BB, or NoCall where A and B symbolically represent the two alleles of a biallelic SNP. However, as evident from copy number, calling algorithm, and pooling-based GWA studies (Pearson et al.; Am J Hum Genet. 2007 January; 80(1):126-39. Epub 2006 Dec. 6.), raw preprocessed data from SNP genotyping arrays is typically in the form of allele intensity measurements that are proportional to the quantity of the "A" and "B" alleles hybridized to a specific probe (or termed features) on a microarray. Individual probe intensity measurements can be derived from the fluorescence measurement of a single bead (e.g. Illumina), micron-scale square on a flat surface (e.g. Affymetrix) or some combination thereof. On a genotyping array, multiple probes are present per SNP at either a fixed number of copies (Affymetrix) or a variable number of copies (Illumina). For example, recent generation Affymetrix arrays typically have 3 to 4 probes specific for the A allele and B allele respectively, whereas Illumina arrays have a random number of probes averaging approximately 18 probes per allele. With 500,000+ SNPs, there are millions of probes (or features) on a SNP genotyping array. While there are considerably different sample preparation chemistries prior to hybridization between SNP genotyping platforms, any of these chemistries can be used, as they should not impact various embodiments disclosed herein.

SNP genotyping algorithms typically begin by transforming normalized data into a ratio or polar coordinates. For simplicity, one can utilize a ratio transformation $Y_j = A_j/(A_j + k_j B_j)$, where $A_j$ is the probe intensity of the A allele and B is the probe intensity of the B allele in the jth SNP. Multiple papers have shown that $Y_j$ transformation approximates allele frequency, where $k_j$ is the SNP specific correction factor accounting for experimental bias and is easily calculated from individual genotyping data. Thus with this transformation, $Y_j$ is an estimate of allele frequency (termed $p_A$) of each SNP. Since most individuals contain two copies of autosomal SNPs, values of the A allele frequency ($p_A$) in a single individual may be 0%, 50%, or 100% for the A allele at AA, AB, or BB, respectively. Equivocally $Y_j$ will be approximately 0, 0.5, or 1, varying from these values due to measurement noise. By example and assuming $k_j=1$, probe intensity measurements of $A_j=450$ and $B_j=550$ yield $Y_j=0.45$ and this SNP would be called AB. In a sample from a single individual, one would thus expect to see a trimodal distribution for Y across all SNPs since only AA, AB, or BB genotype calls are expected. However, in a mixture of multiple individuals, the assumptions of the genotype-calling algorithm are invalid, since only AA, AB, BB, or NoCall are given regardless of the number of pooled chromosomes.

However, one of skill in the art, given the present disclosure, will be able to extract information and meaning from the relative probe intensity data and so be able to use that data to, for example, identify if a subject contributed to the mixture. In some embodiments of the method, one compares allele frequency estimates from a mixture (termed M, where $M_j = A_j/(A_j + k_j B_j)$) to estimates of the mean allele frequencies of a reference population. As used herein, the allele frequency estimates of the mixture are also encompassed within the term sample SNP signature. In addition, as used herein, the mean allele frequency of the reference population is also encompassed within the term reference SNP signature.

The selection of the reference population, where required, is discussed in more detail below. In some embodiments, one assumes that the reference population has a similar ancestral make-up as that of the mixture. This can mean having similar population substructure, ethnicity, and/or ancestral components interchangeably, and define similar ancestral components of an individual or mixture as having similar allele frequencies across all (or substantially all) SNPs.

One can let $Y_{i,j}$ be the allele frequency estimate for the individual i and SNP j, where $Y_{i,j} \in \{0, 0.5, 1\}$, from a SNP genotyping array. The allele frequency estimate for the individual is also encompassed within the term subject SNP signature.

One then compares absolute values of two differences. The first difference $|Y_{i,j}-M_j|$ (which can also be characterized as the absolute value of the sample SNP signature subtracted from the subject SNP signature) measures how the allele frequency of the mixture $M_j$ at SNP j differs from the allele frequency of the individual $Y_{i,j}$ for SNP j (or, put another way, measures how the sample SNP signature differs from the subject SNP signature). The second difference $|Y_{i,j}-Pop_j|$ (which can also be characterized as the absolute value of the reference SNP signature subtracted from the subject SNP signature) measures how the reference population's allele frequency $Pop_j$ differs from the allele frequency of the individual $Y_{i,j}$ for each SNP j (or, put another way, measures how the reference SNP signature differs from the subject SNP signature). The values for $Pop_j$ can be determined from an array of equimolar pooled samples or from databases containing genotype data of various populations. Taking the difference between these two differences, one obtains the distance measure used for individual $Y_i$:

$$D(Y_{i,j}) = |Y_{i,j}-Pop_j| - |Y_{i,j}-M_j| \quad \text{(Equation 1).}$$

As shown in FIG. 1A, under the null hypothesis that the individual is not in the mixture, $D(Y_{i,j})$ approaches zero since the mixture and reference population are calculated to have similar allele frequencies due to having similar ancestral components. Under the alternative hypothesis, $D(Y_{i,j}) > 0$ since one predicts that the $M_j$ is shifted away from the reference population by $Y_i$'s contribution to the mixture. In the case of $D(Y_{i,j}) < 0$, $Y_i$ is more ancestrally similar to the reference population than to the mixture, and thus less likely to be in the mixture. Consistent with the explanation of FIG. 1A, $D(Y_{i,j})$ is positive when $Y_{i,j}$ is closer to $M_j$ and $D(Y_{i,j})$ is negative when $Y_{i,j}$ is closer to $Pop_j$. By sampling numerous SNPs (e.g., 500K+SNPs), one would generally expect $D(Y_{i,j})$ to follow a normal distribution due to the central limit theorem. In some embodiments, one can take a one-sample t-test for the subject, sampled across all (or at least one or more) SNPs, and thus obtain the test statistic:

$$T(Y_i) = (\text{mean}(D(Y_{i,j})) - \mu_0)/(sd(D(Y_{i,j}))/\text{sqrt}(s))) \quad \text{Equation 2}$$

In equation (2) assume $\mu_0$ is the mean of $D(Y_k)$ over individuals $Y_k$ not in the mixture, $sd(D(Y_{i,j}))$ is the standard deviation of $D(Y_{i,j})$ for all SNPs j and individual $Y_i$, and sqrt(s) is the square root of the number of SNPs. In some embodiments, one can set $\mu_0$ at zero since a random individual $Y_k$ should be equally distant from the mixture and the mixture's reference population and so $T(Y_i) = \text{mean}(D(Y_{i,j}))/(sd(D(Y_{i,j}))/\text{sqrt}(s)))$. Under the null hypothesis $T(Y_i)$ is zero and under the alternative hypothesis $T(Y_i) > 0$. In order to account for subtle differences in ancestry between the individual, mixture, and reference populations one can normalize allele frequency estimates to a reference population. If such a large number of SNPs are used that the distribution no longer follows a traditional normal distribution because of correlations between markers, one can also use individuals known not to be within the mixtures to sample distributions in the case that SNPs within linkage disequilibrium are used. In this case, additional methods can also be used to correct and learn the distribution of the test-statistic, such as from the HapMap, and appropriately estimate p-values.

While the above discussion provides an analysis for how data can be compared and analyzed by a frequentist approach, one of skill in the art, given the present disclosure, will appreciate that other approaches are useful as well. For example, as discussed below, a Bayesian approach can be used in some embodiments.

As discussed above and shown below, high-throughput SNP genotyping microarrays have the ability to accurately and robustly resolve whether an individual trace contributions are in a complex genetic material mixture. The following section establishes a probabilistic model and uses Bayesian inference to accurately compare two models: the model where the individual is assumed to be in the mixture and the model where the individual is assumed not to be in the mixture. Using a training dataset one is able to use the raw data for each probe on a microarray instead of using genotypes from a genotyping calling algorithm or other such data transformation. Through a posterior odds ratio comparing the two models, one is able to assess the likelihood of the individual being in the mixture using observations on a genomic scale. With the Bayesian method, one provides further options for using SNPs in identifying individual trace contributors within a test genetic material sample.

As noted above, one challenge in the field of forensics is to identify an individual is present in a highly complex mixture of genomic DNA. As noted herein, this same challenge is present in a variety of other techniques as well, and thus addressing this forensics issue has immediate applications in many other fields. Many methods currently exist that can examine mixtures with a small number of individuals and mixtures composed of thousands of individuals (see, e.g., T. Egeland, I. Dalen, and P. F. Mostad. Estimating the number of contributors to a DNA profile. Int. J. Legal Med., 117:271{275, October 2003; Y. Q. Hu and W. K. Fung. Interpreting DNA mixtures with the presence of relatives. Int. J. Legal Med., 117:39-45, February 2003; and D. J. Balding. Likelihood-based inference for genetic correlation coefficients. Theor Popul Biol, 63:221-230, May 2003). These methods include using short tandem repeats (STR) used to generate DNA profiles, including STRs on the Y chromosome specifically used to identify the male components of the mixture. (see, e.g., T. M. Clayton, J. P. Whitaker, R. Sparkes, and P. Gill. Analysis and interpretation of mixed forensic stains using DNA STR profiling. Forensic Sci. Int., 91:55-70, January 1998; R. G. Cowell, S. L. Lauritzen, and J. Mortera. Identification and separation of DNA mixtures using peak area information. Forensic Sci. Int., 166:28-34, February 2007; M. Bill, P. Gill, J. Curran, T. Clayton, R. Pinchin, M. Healy, and J. Buckleton. PENDULUM{a guideline-based approach to the interpretation of STR mixtures. Forensic Sci. Int., 148:181-189, March 2005; M. A. Jobling and P. Gill. Encoded evidence: DNA in forensic analysis. Nat. Rev. Genet., 5:739-751, October 2004. Methods using Mitochondrial DNA (mtDNA)) are useful when analyzing severely degraded DNA and can be used jointly with STRs. Goodwin, A. Linacre, and P. Vanezis. The use of mitochondrial DNA and short tandem repeat typing in the identification of air crash victims. Electrophoresis, 20:1707-1711, June 1999). A number of methods have also investigated using a very small number of SNPs with mtDNA to mitigate specific problems with mtDNA (M. D. Coble, R. S. Just, J. E. O'Callaghan, I. H. Letmanyi, C. T. Peterson, J. A. Irwin, and T. J. Parsons. Single nucleotide polymorphisms over the entire mtDNA genome that increase the power of forensic testing in Caucasians. Int. J. Legal Med., 118:137-146, June 2004; T. J. Parsons and M. D. Coble. Increasing the forensic discrimination of mitochondrial DNA testing through analysis of the entire mitochondrial DNA genome. Croat. Med. J., 42:304-309, June 2001; R. S. Just, J. A. Irwin, J. E. O'Callaghan, J. L. Saunier, M. D. Coble, P. M. Vallone, J. M. Butler, S. M. Barritt, and T. J. Parsons. Toward increased utility of mtDNA in forensic identifications. Forensic Sci. Int., 146 Suppl:S147-149, December 2004; and P. M. Vallone, R. S. Just, M. D. Coble, J. M. Butler, and T. J. Parsons. A multiplex allele specific primer extension assay for forensically informative SNPs distributed throughout the mitochondrial genome. Int. J. Legal Med., 118:147-157, June 2004) but have not investigated SNPs exclusively on the genomic scale as the determining factor for inclusion in a complex mixture. Recently, Homer et al. (Homer et al. Resolving individuals contributing trace amounts of DNA to highly complex mixtures using high-density snip genotyping microarrays, the entirety of which is hereby incorporated by reference) and the present disclosure presented herein have demonstrated that high-throughput SNP genotyping microarrays have the ability to accurately and robustly resolve whether an individual trace contributions are in a complex genomic DNA mixture. This genomic approach does not target specific sequences, regions or small number of polymorphisms, but instead can employ multiplex experiments performed on SNP microarrays to resolve whether an individual is present in a complex mixture. In some embodiments, this method also does not rely on knowing the number of individuals in the mixture. SNP microarrays have been widely used in Genome-wide Association studies, and when applied to Forensics SNP microarrays over a level of multiplexing not previously found in other methods. Nevertheless, Homer et al. (and the results discussed above and in Example 1) provide a frequentist approach based on cumulative shifts of relative allele signals across all SNPs to provide a significance value for the null hypothesis, where the individual is assumed not to be in the mixture. In some embodiments, two microarrays can be run, one using DNA from the individual of interest and one using the pool of DNA from the mixture. This allows one to use a reference population for comparison, allowing one to accurately identify if an individual is present in the mixture. Additionally, this can be achieved even if a relative's DNA was used as a proxy for the individual of interest. Although such an embodiment performs well for many complex mixtures, other approaches can be used and as such, a probabilistic model is presented in the following section.

Bayesian

The following section discloses a probabilistic model based on the total observations at the raw intensity level for SNP microarrays to accurately assess the likelihood that the individual of interest (e.g., subject) is or is not in the complex mixture (e.g., test genetic material sample). Additionally, a training dataset was used to estimate the probability distribution of the raw intensity level observations. Two models were compared, one where the individual of interest is assumed to be in the mixture, and another where the individual of interest is assumed not to be in the mixture, in the form of a posterior odds ratio. The likelihood of each of the two models was derived using Bayesian inference to accurately assess the probability of the observations. With this embodiment, a more robust and accurate model of the observations was created, giving a better statistical measure of evidence. As the number of SNPs available on current microarray technologies continues to increase, so will the accuracy of various embodiments of the method to identify the contribution of an individual to a highly complex mixture.

Models

Two Competing Models

The modeling is performed to identify whether or not an individual is present within a given complex mixture. Therefore one can examine the odds ratio between two competing models, one where the individual is assumed to be in the mixture (denoted $\theta_A$) and one where the individual is assumed not to be in the mixture (denoted $\theta_\varnothing$). There are two distinct observations, one set of observations from the individual of interest and one set of observations from the complex mixture. The observations for the individual of interest are denoted as $\vec{x}$ and the observations for the complex mixture were denoted as $\vec{y}$ for all s SNPs. For SNP i the observation $x_i$ for the individual of interest (e.g., subject) is a raw intensity value, and the observation $y_i$ for the complex mixture is similarly defined.

On a given microarray there are typically multiple probes per SNP as well as pairs of intensity values per probe. One can choose to treat probe value (a pair of intensity values) separately or combine the probes into a single measure. For this analysis, the probe values can be combined by taking the mean probe value over all probes, and combing the pair of intensity values into a simple ratio of the two values. For example if one had the intensity pair X and Y one can use the ratio $$\frac{X}{X+Y}$$

or for a more elegant ratio of arctan $$\left(\frac{Y}{X}\right).$$

Nevertheless, combing the intensity values in this manner has been used in previous studies using complex mixtures of DNA, namely pooling-based Genome-wide Association studies (J. V. Pearson, M. J. Huentelman, R. F. Halperin, W. D. Tembe, S. Melquist, N. Homer, M. Brun, S. Szelinger, K. D. Coon, V. L. Zismann, J. A. Webster, T. Beach, S. B. Sando, J. O. Aasly, R. Heun, F. Jessen, H. Kolsch, M. Tsolaki, M. Daniilidou, E. M. Reiman, A. Papassotiropoulos, M. L. Hutton, D. A. Stephan, and D. W. Craig. Identification of the genetic basis for complex disorders by use of pooling-based genomewide single-nucleotide-polymorphism association studies. Am. J. Hum. Genet., 80:126-139, January 2007) and this method was adopted.

To compare the two models the posterior odds ratio $$\frac{Pr(\vec{y}|\vec{x},\theta_A)}{Pr(\vec{y}|\vec{x},\theta_\emptyset)}$$

was examined. If the odds ratio is large, then this gives evidence that the individual of interest is in the mixture. If the odds ratio is small, then this gives evidence that the individual of interest is not in the mixture. In this manner one is able to resolve whether the individual is present within the complex mixture.

Likelihoods

Suppose one had s SNPs, one denotes the observations as $\vec{y}=(y_1, \ldots, y_s)$ and $\vec{x}=(x_1 \ldots x_s)$. Nevertheless, to formulate a likelihood correctly a number of hidden variables should be known. Let $\eta+2$ be the number of chromosomes in the mixture. Since each individual in the mixture contributes two chromosomes, $\eta$ is a multiple of two. For each SNP i, suppose one has the two alleles A and B. One should then know the number of A alleles in the mixture $\kappa_i$ and the number of A alleles in the person of interest $\beta_i$. Since by definition $\eta$, $\kappa_i$, and $\beta_i$ are hidden, to compute the likelihood of either model one should sum over all possible values for these three hidden variables. For consistency Greek letters for hidden variables and alphabet letters for observed variables were used.

Training Dataset

Given the observed and hidden variables more information is useful to accurately compute the likelihoods. Since one has raw intensity values instead of genotypes for both the mixture and the person of interest, one should know the conditional probability $Pr(R_i=r_i|\Gamma_i=\gamma_i)$ for $\gamma_i \in \{0, 1, 2\}$. This is the conditional probability that for SNP i the relative intensity value is $r_i$ given the hidden unordered genotype is i where denote the unordered genotype A/A to be 0, A/B to be 1, and B/B to be 2. Again one does not know $\gamma_i$ for each SNP i and each individual in the mixture or for the individual of interest but in this case one can estimate the distribution of these probabilities by using a training dataset, from the HapMap Project (The International HapMap Project. Nature, 426:789-796, December 2003). From the HapMap Project one is able to obtain for a given individual both the consensus genotype calls and raw intensity values for each SNP on the Affymetrix 5.0 platform. The HapMap project has this information for 270 individuals from four distinct populations. Additionally, the genotypes for each SNP were not only derived from the corresponding raw intensity values but also from other microarray platforms and replicate experiments resulting in a consensus genotype call for each SNP. This gives one further assurance that the genotype call is correct.

Therefore for each SNP i one can plot three distributions for $r_i$ given each of the possible unordered genotype $\gamma_i$. To simplify, one assumes that each of the three distributions $Pr(R_i=r_i|\Gamma_i=0)$, $Pr(R_i=r_i|\Gamma_i=1)$, and $Pr(R_i=r_i|\Gamma_i=2)$ follow normal distributions $N(\mu_0, \sigma_0)$, $N(\mu_1, \sigma_1)$, and $N(\mu_2, \sigma_2)$ respectively. One can estimate $\mu_0, \mu_1, \mu_2, \sigma_0, \sigma_1, \sigma_2$ easily from the training data set and use these parameters in the calculation of the likelihoods.

Finally, this training data set gives, for each SNP i, the population allele frequency of A denoted $p_i$. It is useful when selecting the training dataset population to consider the ancestry of the population since allele frequencies can vary over population, and therefore introduce systematic biases in the model. Nevertheless, if SNPs used in the likelihood calculations are chosen to be ancestrally unbiased and unlinked, one avoids an admixture problem and can treat each SNP independently.

Computing the likelihood of $\theta_\emptyset$;

First, the model $\theta_\emptyset$ with the assumption that the person of interest is not in the mixture, is examined. Therefore the likelihood of $\theta_\emptyset$; is just $Pr(\vec{\gamma}|\vec{x}, \theta_\emptyset)$. Since one does not observe the number of chromosomes in the mixture $\eta$ one can sum over all possible values of $\eta$.

$$Pr(\vec{y}|\vec{x},\theta_\emptyset) = \sum_{\eta=0}^{\infty} I_{\{\eta \% 2=0\}} Pr(\vec{y}|\eta,\vec{x},\theta_\emptyset) Pr(\eta|\vec{x},\theta_\emptyset)$$

where $I_{\{\eta \% 2=0\}}$ is one if $\eta$ is a multiple of two, zero otherwise. One can assume an uninformative (uniform) prior for $\eta$ as well as setting a limit on the maximum value for $\eta$ given the specific scenario. Therefore one lets $Pr(\eta|\vec{x}\theta_\emptyset)$ be uniform over all values of $\eta$.

Since each SNP was defined to be independent one can simply examine each SNP i independently and take the product over the probabilities for each SNP so that $$Pr(\vec{y}|\eta,\vec{x},\theta_\emptyset) = \prod_{i=0}^{s} Pr(y_i|\eta,x_i,\theta_\emptyset)$$

To calculate $Pr(\vec{y}_i|\eta,x_i,\theta_\varnothing)$ one should know the number of A alleles in the mixture, denoted $\kappa_i$. Since $\kappa_i$ is hidden one can simply sum over all possible values of $\kappa_i$. In the $\theta_\varnothing$ model, the individual of interest is not in the mixture so $\kappa_i$ can range from 0 to $\eta+2$ giving $$Pr(y_i \mid \eta, x_i, \theta_\varnothing) = \sum_{\kappa_i=0}^{\eta+2} Pr(y_i \mid \kappa_i, \eta, x_i, \theta_\varnothing) Pr(\kappa_i \mid \eta, x_i, \theta_\varnothing)$$

One assumes that $Pr(\kappa_i|\eta,x_i,\theta_\varnothing)$ follows a binomial distribution $B(\eta+2; p_i)$ where $p_i$ is the allele frequency of allele A obtained from the training dataset. Therefore one has $$Pr(\kappa_i \mid \eta, x_i, \theta_\varnothing) = \binom{\eta+2}{\kappa_i} p_i^{\kappa_i}(1-p_i)^{((\eta+2)-\kappa_i)}$$

Additionally, one does not directly observe the number of A alleles for the individual of interest $\beta_i$ so one simply sums over all possible values of $\beta_i$ giving $$Pr(y_i \mid x_i, \eta, \kappa_i, \theta_\varnothing) = \sum_{\beta_i=0}^{2} Pr(y_i \mid \beta_i, \eta, \kappa_i, \theta_\varnothing) Pr(\beta_i \mid x_i, \eta, \kappa_i, \theta_\varnothing)$$

To calculate the final two probabilities $Pr(y_i|\beta_i,\eta,\kappa_i,\theta_\varnothing)$ and $Pr(\beta_i|x_i,\eta,\kappa_i,\theta_\varnothing)$ one uses the three probability distributions estimated from the training dataset: $Pr(R_i=r_i|\Gamma_i=0)$, $Pr(R_i=r_i|\Gamma_i=1)$, and $Pr(R_i=r_i|\Gamma_i=2)$. Since it was assumed that these three distributions were normally distributed one has that $Pr(y_i|\beta_i,\eta,\kappa_i,\theta_\varnothing)=Pr(y_i|\eta,\kappa_i,\theta_\varnothing)=\mathbb{N}(\mu_{\lambda_i},\sigma_{\lambda_i})$ Here one has that $$\lambda_i = \frac{\kappa_i}{(\eta+2)}.$$

To smoothly interpolate between the three different distributions, if $\lambda_i>0.5$ then $\mu_{\lambda_i}=\mu_2(2\lambda_i-1)+\mu_1(2-2\lambda_i)$, and if $\lambda_i\leq 0.5$ then $\mu_{\lambda_i}=\mu_1(2\lambda_i)+\mu_0(1-2\lambda_i)$ For the second probability one similarly has $Pr(\beta_i|x_i,\eta,\kappa_i,\theta_\varnothing)=Pr(\beta_i|x_i)=\mathbb{N}(\mu_{\beta_i},\sigma_{\beta_i})$ Since $\beta_i$ is zero, one, or two one knows which distribution to use because one can infer the unordered genotype from $\beta_i$. If $\beta_i=0$ then $\mu_{\beta_i}=\mu_0$ and $\sigma_{\beta_i}=\sigma_0$, if $\beta_i=1$ then $\mu_{\beta_i}=\mu_1$ and $\sigma_{\beta_i}=\sigma_1$, and if $\beta_i=2$ then $\mu_{\beta_i}=\mu_2$ and $\sigma_{\beta_i}=\sigma_2$.

Computing the Likelihood of $\theta_A$

Next one examines the model $\theta_A$ with the assumption that the person of interest is in the mixture. Therefore the likelihood of $\theta_A$ is just $Pr(\vec{y}|\vec{x},\theta_A)$. Since one does not observe the number of chromosomes in the mixture $\eta$ one should sum over all possible values of $\eta$.

$$Pr(\vec{y} \mid x, \theta_A) = \sum_{\eta=0}^{\infty} I_{\{\eta \% 2=0\}} Pr(\vec{y} \mid \eta, \vec{x}, \theta_A) Pr(\eta \mid \vec{x}, \theta_A)$$

where $I_{\{\eta \% 2=0\}}$ is one if $\eta$ is a multiple of two, zero otherwise. Similar to the $\theta_\varnothing$ model one can assume an uniformative (uniform) prior for $\eta$ as well as setting a limit on the maximum value for $\eta$ given the specific scenario. Therefore one lets $Pr(\eta|\vec{x},\theta_A)$ be uniform over all values of $\eta$.

Since each SNP was defined to be independent one can simply examine each SNP i independently and take the product over the probabilities for each SNP so that $$Pr(\vec{y} \mid \eta, \vec{x}, \theta_A) = \prod_{i=0}^{s} Pr(y_i \mid \eta, x_i, \theta_A)$$

Under the $\theta_A$ model one assumes that the individual of interest is in the mixture. Therefore unlike the $\theta_\varnothing$ model one has that the number of A alleles in the mixture is partly dependent on $\beta_i$. Therefore one first sums over all possible values for $\beta_i$:

$$Pr(y_i \mid \eta, x_i, \theta_A) = \sum_{\beta_i=0}^{2} Pr(y_i \mid \beta_i, \eta, \theta_A) Pr(\beta_i \mid \eta, x_i, \theta_A)$$

One assumes that the individual of interest (e.g., subject) contributes two chromosomes to the mixture. Thus when one sums over all possible values of $\kappa_i$ one allows $\kappa_i$ to range from 0 to $\eta$, excluding two the two chromosomes determined by $\beta_i$. Therefore one has that $$Pr(y_i \mid \beta_i, \eta, \theta_A) = \sum_{\kappa_i=0}^{\eta} Pr(y_i \mid \kappa_i, \beta_i, \eta, \theta_A) Pr(\kappa_i \mid \eta, \beta_i, \theta_A)$$

One assumes that $Pr(\kappa_i|\eta,\beta_i,\theta_A)$ follows a binomial distribution $\mathbb{B}(\eta,p_i)$ where $p_i$ is the allele frequency of allele A obtained from the training dataset. Therefore one has $$Pr(\kappa_i \mid \eta, \beta_i, \theta_A) = \binom{\eta}{\kappa_i} p_i^{\kappa_i}(1-p_i)^{(\eta-\kappa_i)}$$

Finally, similar to the $\theta_\varnothing$ model find the probabilities $Pr(y_i|\kappa_i,\beta_i,\theta_A)$ and $Pr(\beta_i|\eta, x_i,\theta_A)$ be using the three probability distributions obtained from the training dataset:

$Pr(R_i=r_i|\Gamma_i=0)$, $Pr(R_i=r_i|\gamma_i=1)$, and $Pr(R_i=r_i|\Gamma_i=2)$ Therefore one has that $$Pr(y_i|\kappa_i,\beta_i,\eta,\theta_A) = Pr(y_i|\eta,\kappa_i,\theta_A) = \mathbb{N}_{(\mu_{\lambda_i},\sigma_{\lambda_i})}$$

Here one has that $$\lambda_i = \frac{\kappa_i + \beta_i}{(\eta + 2)}.$$

This definition of $\lambda_i$ differs from the one under the $\theta_\varnothing$; model since one now has conditioned on the individual of interest contributing $\beta_i$ A alleles. Similar to $\theta_\varnothing$, one smoothly interpolates between the three different distributions, if $\lambda_i > 0.5$ then $\mu_{\lambda,i} = \mu_2 (2\lambda_i - 1) + \mu_1(2 - 2\lambda_i)$ and if $\lambda_i < 0.5$ then $\mu_{\lambda,i} = \mu_1 (2\lambda_i) + \mu_0 (1 - 2\lambda_i)$.

For the second probability one similarly has $$Pr(\beta_i|\eta,x_i,\theta_A) = Pr(\beta_i|x_i) = \mathbb{N}_{(\mu_{\beta_i},\sigma_{\beta_i})}$$

Since $\beta_i$ is zero, one or two one knows which distribution to use because one can infer the unordered genotype from $\beta_i$. If $\beta_i = 0$ then $\mu_{\beta,i} = \mu_0$ and $\sigma_{\beta,i} = \sigma_0$, if $\beta_i = 1$ then $\mu_{\beta,i} = \mu_1$ and $\sigma_{\beta,i} = \sigma_1$, and if $\beta_i = 2$ then $\mu_{\beta,i} = \mu_2$ and $\sigma_{\beta,i} = \sigma_2$.

Computational Complexity

One first observes that computing the probability mass function of the binomial distribution is not a constant operation and depends both on $\eta$ and $\kappa_i$ in the specific application. Naively this is dominated by $\eta$ multiplications (of $p_i$ and $(1-p_i)$ combined) and the term $$\frac{(\eta + 2)}{\kappa_i},$$

which in the worst case requires $O(\eta)$ operations. One also can compute the probability mass function of the normal distribution. Let the time to compute this be $$\mathbb{N}_t$$

Let $\eta_l$ be the maximum value for $\eta_l$, then it is then easy to see that the time to compute $\theta_\varnothing$ or $\theta_A$ is simply $$= \sum_{\eta=0}^{\eta_l} \sum_{i=0}^{s} \sum_{\kappa_i=0}^{\eta+2} \mathbb{N}_t O(\eta)$$

$$= \sum_{\eta=0}^{\eta_l} s \cdot \mathbb{N}_t \cdot O(\eta^2)$$

$$= s \cdot \mathbb{N}_t \cdot O(\eta_l^3)$$

The space complexity for this algorithm is $O(1)$ since one can examine each SNP independently.

Extensions

A factor of the above model is the practical implementation. When computing these probabilities it is clear that some of probabilities calculated above may approach zero and therefore be $-\infty$ when calculated in log space. It is useful that when computing these probabilities that care is taken to perform the computations in log space without introducing errors.

There are a number of extensions to this method that can improve the model. Firstly, one can make sure to select a set of SNPs that are independent since one treats each SNP independently in the calculation. For example, on the Affymetrix 5.0 SNP microarray platform there are approximately 500,000 SNPs. To ensure that SNPs are not correlated, the resulting set of SNPs is approximately one-tenth the size of the original set. To be sure, one is throwing out a lot of redundant and useful information. An extension of the method is not to assume independence between SNPs and instead adjust for the correlation between SNPs, thus utilizing the full set of SNPs present on current microarray platforms.

One also implicitly assumes that the mixture and individual of interest have the same ancestral make-up as the training dataset. For example, if the individual of interest and mixture are ancestrally native American, one may lose power if one uses a Caucasian or Asian training dataset. To correct for this problem, one can choose training datasets that rejects the ancestry of the mixture and individual of interest. Additionally, one can also choose SNPs whose allele frequency does not vary across populations.

Since one assumes that the probability of $\kappa i$ is binomially distributed, one implicitly assumes Hardy-Weinberg Equilibrium (HWE). This is not true for many SNPs and one can take care when calculating the allele frequency pi from the training set. One could instead test for HWE for each SNP by using a training dataset and exclude a certain percentage of SNPs from further analysis.

In the analysis for each SNP, multiple probes were combined and for each probe the relative intensity values were combined. To extend the method and to completely use the raw data values, one can treat the probes as multiple identically distributed observations for the given snip, and treat each intensity value for the probe separately. Therefore when one computes $Pr(R_i = r_i | \Gamma_i = \gamma_i)$ one would have six distributions instead of three rejecting the fact that the intensity values for each allele were treated separately.

In the above section, a probabilistic model was established for identifying trace contributions of an individual within a complex DNA mixture. Previous methods relied on sequencing or probing small portions of DNA or mtDNA (T. Egeland, I. Dalen, and P. F. Mostad. Estimating the number of contributors to a DNA profile. Int. J. Legal Med., 117: 271{275, October 2003; Y. Q. Hu and W. K. Fung. Interpreting DNA mixtures with the presence of relatives. Int. J. Legal Med., 117:39-45, February 2003; D. J. Balding. Likelihood-based inference for genetic correlation coefficients. Theor Popul Biol, 63:221-230, May 2003; T. M. Clayton, J. P. Whitaker, R. Sparkes, and P. Gill. Analysis and interpretation of mixed forensic stains using DNA STR profiling. Forensic Sci. Int., 91:55-70, January 1998; R. G. Cowell, S. L. Lauritzen, and J. Mortera. Identification and separation of DNA mixtures using peak area information. Forensic Sci. Int., 166:28-34, February 2007; M. Bill, P. Gill, J. Curran, T. Clayton, R. Pinchin, M. Healy, and J. Buckleton. PENDULUM{a guideline-based approach to the interpretation of STR mixtures. Forensic Sci. Int., 148:181-189, March 2005; M. A. Jobling and P. Gill. Encoded evidence: DNA in forensic analysis. Nat. Rev. Genet., 5:739-751, October 2004; W. Goodwin, A. Linacre, and P. Vanezis. The use of mitochondrial DNA and short tandem repeat typing in the identification of air crash victims. Electrophoresis, 20:1707-1711, June 1999; M. D. Coble, R. S. Just, J. E. O'Callaghan, I. H. Letmanyi, C. T. Peterson, J. A. Irwin, and T. J. Parsons. Single nucleotide polymorphisms over the entire mtDNA genome that increase the power of forensic testing in Caucasians. Int. J. Legal Med., 118:137-146, June 2004; T. J. Parsons and M. D. Coble. Increasing the forensic discrimination of mitochondrial DNA testing through analysis of the entire mitochondrial DNA genome. Croat. Med. J., 42:304-309, June 2001; R. S. Just, J. A. Irwin, J. E. O'Callaghan, J. L. Saunier, M. D. Coble, P. M. Vallone, J. M.

Butler, S. M. Barritt, and T. J. Parsons. Toward increased utility of mtDNA in forensic identifications. Forensic Sci. Int., 146 Suppl:S147-149, December 2004; and P. M. Vallone, R. S. Just, M. D. Coble, J. M. Butler, and T. J. Parsons. A multiplex allele specific primer extension assay for forensically informative SNPs distributed throughout the mitochondrial genome. Int. J. Legal Med., 118:147-157, June 2004) and did not use the whole genome (or genome wide analysis) to answer this. With the increasing density and decreasing price of current SNP microarray technologies, it is feasible to probe over a million SNPs for under one-thousand dollars and thus giving a genomic perspective on this problem.

The above analysis leverages the number of SNPs on the microarrays to accurately assess the probability that an individual of interest (e.g., subject) is present within a highly complex mixture. Since the number of SNPs on microarrays is now over one-million, one is able to obtain a sufficient number of observations to determine inclusion when compared to previous methods. This embodiment of the method specifically computes the posterior odds ratio between two models. The first model assumes the individual of interest is not present in the mixture and the second model assumes the individual of interest is present in the mixture. One then derives a likelihood function for both models given the observations of the mixture and individual of interest. A training dataset is used to provide for each SNP probability distributions for the observed probe intensity values given the unordered genotypes. While the above Bayesian approach demonstrates some embodiments for performing the comparison or methods described herein, these processes or steps are not required for all of the embodiments described herein. While the above description (and below demonstration of the above described process) establishes the proof of concept and functionality of various embodiments of the invention, one of skill in the art will appreciate that there are a wide variety of techniques or operations by which the general method can be performed and how it can be put to practical use. While only a summary of some of the possible embodiments, FIG. 1B depicts a more schematic representation of how the genetic material matching techniques described herein can be employed.

Figure 1B:
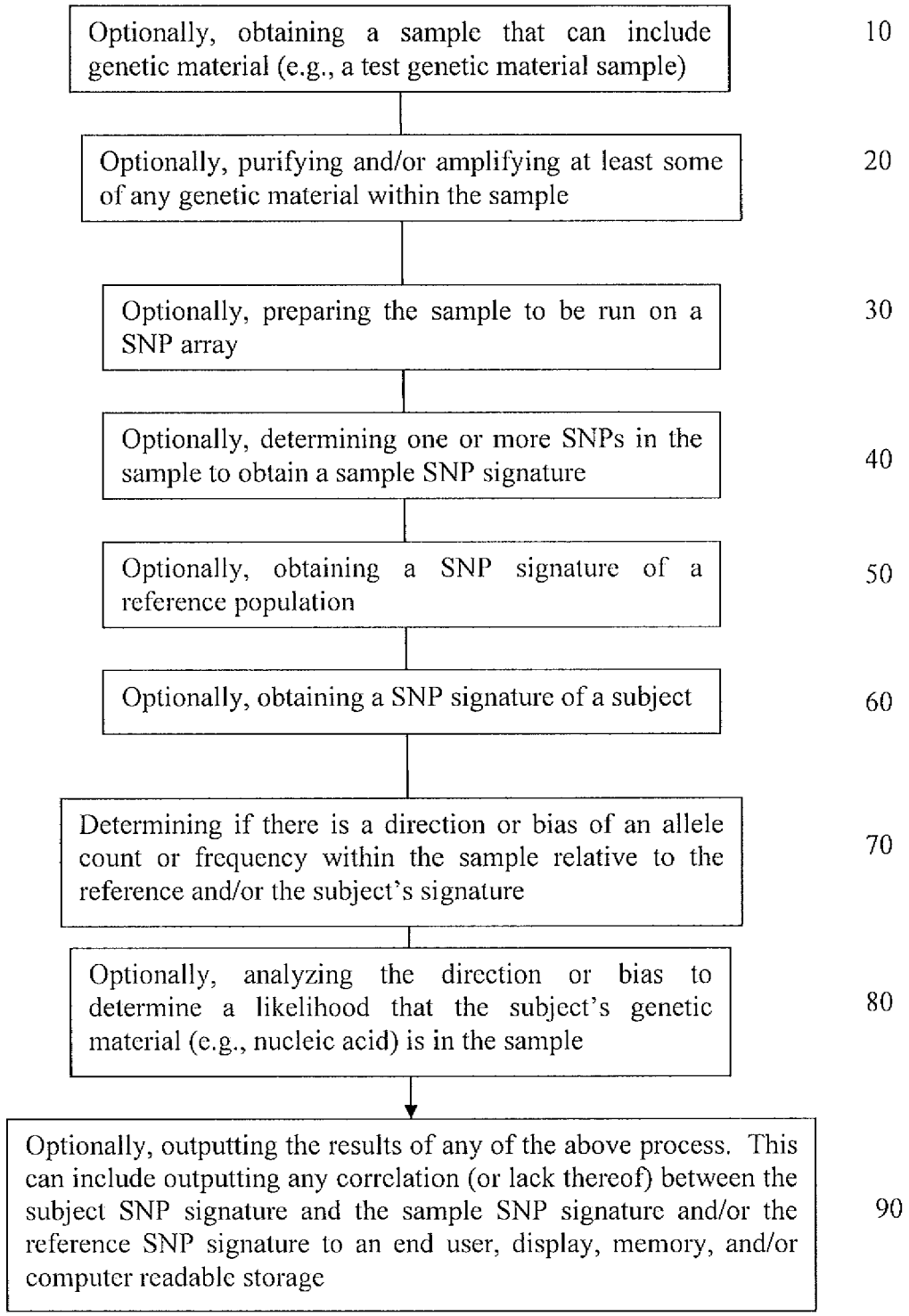
FIG. 1B is a flow chart depicting various possible processes involved in some embodiments described herein.

As shown in FIG. 1B, in some embodiments, one can initially start some of the embodiments described herein by optionally obtaining a sample that can (but need not) include genetic material (e.g., a test genetic material sample) as shown in process 10. One can then, optionally, purify and/or amplify at least some of any genetic material within the sample as shown in process 20. One can then, optionally, prepare the sample to be run on a SNP array as shown in process 30. One can then, optionally, determine one or more SNPs in the sample to obtain a sample SNP signature as shown in process 40. One can then, optionally, obtain a SNP signature of a reference population as shown in process 50. This SNP signature can be, for example, created by a SNP analysis of a reference population, or obtainable in data form. One can then, optionally, obtain a SNP signature of a subject, as shown in process 60. One can then determine if there is a direction or bias of an allele count and/or frequency within the sample relative to the reference and/or the subject's signature as shown in process 70. One can then, optionally, analyze the direction or bias to determine a likelihood that the subject's genetic material is in the sample as shown in process 80. One can, optionally, have any of the results from the above processes output to an end user or memory 90. In some embodiments, one can, optionally, output any correlation (or lack thereof) between the subject SNP signature and the sample SNP signature and/or the reference SNP signature to an end user, display, memory, and/or computer readable storage. In some embodiments, this information is output or provided to the subject.

In some embodiments, any one of more of the processes in FIG. 1B are performed by a module configured to perform the process, which, optionally, can be part of a system. Thus, in some embodiments, FIG. 1B also represents modules that are capable of performing the steps for optionally obtaining a sample that can (but need not) include genetic material (e.g., a test genetic material sample) as in 10; a module to optionally purify and/or amplify at least some of any genetic material within the sample as shown in 20; a module to optionally prepare the sample to be run on a SNP array as shown in 30; a module to optionally determine one or more SNPs in the sample to obtain a sample SNP signature as shown in 40; a module to obtain a SNP signature of a reference population as shown in 50; a module to optionally obtain a SNP signature of a subject, as shown in 60; a module to determine if there is a direction or bias of an allele count and/or frequency within the sample relative to the reference and/or the subject's signature as shown in 70; a module to optionally analyze the direction or bias to determine a likelihood that the subject's genetic material is in the sample as shown in 80; a module to optionally have any of the results from the above output to an end user or memory 90. It will be understood, however, that this illustration is merely exemplary and that such modules or components can be executed on a plurality of computing devices, on one or more virtual machines, as stand-alone components, or the like.

In some embodiments, one also has a module to output any correlation (or lack thereof) between the subject SNP signature and the sample SNP signature and/or the reference SNP signature to an end user, display, memory, and/or computer readable storage. In some embodiments, this information is output or provided to the subject. In some embodiments, the system comprises an input module, to input one or more SNP signatures; a processing module, to compare the two or more SNP signatures; and an output module, to output the comparison. In some embodiments, any one or more of the above modules are executed on one or more computing devices. In addition, methods and functions described herein are not limited to any particular sequence, and the blocks or states relating thereto can be performed in other sequences that are appropriate. For example, described blocks or states may be performed in an order other than that specifically disclosed, or multiple blocks or states may be combined in a single block or state.

While a likelihood determination is one useful way of displaying any present correlation between the genetic material in the test genetic material sample and the subject's genetic material, any other way of displaying the correlation between the subject's genetic material and the test genetic material sample and/or the reference population's genetic material can also be used and output to an end user or memory.

Appendix A is a computer programming listing appendix, which is attached hereto to and is to be considered part of this specification. It provides some embodiments of code files usable for executing some embodiments of the processes and/or modules provided herein. The first code in Appendix A is Both the code in Appendix A and the electronic version of the computer programming listing appendix are nonlimiting examples of the code that can be employed for some of the present embodiments. The code need not include any or all of the code listed in either Appendix A at the end of the specification or the electronic version of the computer programming listing appendix. In some embodiments, the computer programming comprises, consists, or consists essentially of pages 72-155 of Appendix A.

Variations on Embodiments

In some embodiments, a method for determining likelihood that a subject contributed genetic material to a test genetic material sample is provided. In some embodiments, one tests whether a POI is in the mixture by assessing the probability that the allele frequency of the mixture is biased towards the POI, as compared to one or more reference populations.

Methods and functions described herein are not limited to any particular sequence, and the blocks or states relating thereto can be performed in other sequences that are appropriate. For example, described blocks or states may be performed in an order other than that specifically disclosed, or multiple blocks or states may be combined in a single block or state.

Complex Mixtures

In some embodiments, a complex genetic material mixture (or test genetic material sample) is one that includes genetic material (such as DNA) derived from more than one source. A complex mixture can also contain compounds, the presence of which causes experimental noise that could mask identification in some techniques, such as STR analysis.

In some embodiments, the invention involves a method of rapidly and sensitively determining whether a trace amount (<1%) of genomic DNA from an individual source is present within a complex DNA mixture.

In some embodiments, the test genetic material sample includes a compound that would prevent or complicate STR analysis. In some embodiment, test genetic material sample includes a molecule that degrades nucleic acids. In some embodiments, the test genetic material sample includes proteins and/or enzymes. In some embodiments, the test genetic material sample includes mRNA, RNA, siRNA, and/or DNA.

In some embodiments, the mixture includes, or is suspected of including genetic material/nucleic acids from more than one human, for example, 2, 3, 4, 5, 6, 7, 8, 9, 10, 20, 30, 40, 50, 60, 80, 100, 150, 200, 300, 500, 1000, 10,000 humans or more, including any amount defined between any two of the preceding values or any amount greater than any one of the preceding values.

In some embodiments, the subject's genetic material in the test genetic material sample is, or is suspected of being the source of less than 100% of the genetic material, for example, less than 100%, 99, 98, 95, 90, 80, 70, 60, 50, 40, 30, 20, 10, 5, 1, 0.5, 0.1, 0.05, 0.01, 0.005, 0.001, 0.0005, 0.0001 percent or less of the sample's genetic material is from the subject, including any amount defined between any two of the preceding values or any amount greater than any one of the preceding values.

Sample Preparation

In some embodiments, while STR analysis might otherwise require additional manipulation of a target for analysis of the sample, a test genetic material sample need only be manipulated enough to allow for the application of the sample onto a SNP array In some embodiments, one could expect that it would be acceptable to have SNP drop-out due to the large number of SNPs available for testing. That is if only 10% of 500,000 SNPs are able to give reliable calls, the 50,000 SNPs are more than sufficient to reliably evaluate a mixture. By comparison, if only 2 of 13 STRs are available there is generally little ability to resolve the mixture.

In some embodiments, a PCR reaction is performed on the genetic material (reference, subject, and/or test genetic material sample). In some embodiments, this can be a simple PCR reaction, although any method that amplifies the desired genetic material can be used. In some embodiments, primers for the amplification reaction are included in or as part of a kit for the present method. The primers can be selected so as to amplify desired sections of the genetic material to selectively amplify the SNPs to be examined. In some embodiments, the same primers can be used on one or more of the samples from the reference, subject, and test genetic material sample to increase the likelihood that the same SNPs are being reviewed.

In some embodiments, the use of one or more the methods described herein allows one to reduce the manipulation of the sample (reference, subject, and/or test genetic material sample) prior to examining it to prepare a SNP signature. In some embodiments, impurities that would otherwise complicate a STR analysis are not removed for the SNP analysis.

Sources of Genetic Material

Sources can include human beings, pets, mammals, birds, reptiles, amphibians, other animals, various cell types, algae, slime mold, mollusks, plants, bacteria, viruses, and any other organism that contains genetic material, such as DNA, whether terrestrial or extraterrestrial.

Probes

In some embodiments, the SNP probes are selected so as to reduce any undesirable cross-hybridization. In some embodiments, cross-hybridization is addressed by normalizing markers using a quantile normalization approach, and/or by direct measurement of an individual who is homozygote for a given allele. In some embodiments, the probes are random probes. In some embodiments, the probes are those that will hybridize to genetic material that is linked to or similar to standard STR forensics markers. In some embodiments, the probes allow for examination of genetic material that would be examined via restriction fragment length polymorphism, PCR analysis, STR analysis, mitochondrial DNA analysis and/or Y-chromosome analysis. In some embodiments, the probes probe genetic material related, the same as, or linked to the 13 specific STR regions for COD'S. In some embodiments, the probes reveal information regarding one or more of the following STR locus: D3S1358, vWA, FGA, D8S1179, D21S11, D18551, D5S818, D13S317, D7S820, CSF1PO, TPDX, THO1, and/or D16S539. In some embodiments, SNPs that are near the above and/or other known STRs are employed. In some embodiments, SNPs that track the above or other known STRs are employed.

In some embodiments, the number and variance of the probes is selected based upon the results presented in Example 1, outlining probe variance, probe number, and the number of people in the mixture.

Kits

In some embodiments, the devices, parts, subparts, or methods described herein can be combined into a kit for practicing any of the disclosed techniques. In some embodiments, any of the methods can be provide in written format (such as in a set of instructions), or on a computer readable media. In some embodiments, any of the steps or processes described herein that are capable of being executed by a machine can be provided on a computer readable media. In some embodiments, programming that obtains the various SNP signatures can be provided. In some embodiments, programming that compares the various SNP signatures can be provided (such as executing any of the equations provided herein). In some embodiments, programming that outputs a likelihood that a subject contributed to a test genetic material sample is provided. Any such programming can be on computer readable media and/or downloadable from an online source.

In some embodiments, the kit includes one or more primers for SNP amplification. In some embodiments, the SNPs, and thus the primers, are specific for regions useful in forensics. In some embodiments, a large number of SNP primers are used, for example, more than 100, such as 101, 200, 500, 1000, 2000, 5000, 10,000, 20,000, 30,000, 40,000, 50,000, 60,000, 70,000, 80,000, 90,000, or more SNPs, including any amount defined between any two of the preceding values and any range greater than any one of the preceding values.

In some embodiments, the kits include one or more reference SNP signatures. Such SNP signatures can be stored on computer readable media or downloadable from a website. In some embodiments, the reference populations are identified by groups such that the appropriate reference population can be matched with the subject and/or test genetic material sample. In some embodiments, the kit includes one or more subject SNP signatures. Such SNP signatures can include, for example, the SNP signatures of a selection of convicted felons. In some embodiments, reference SNP signatures can include general selections from the population. In some embodiments, reference SNP signatures are configured for cell selection, biopsies, or any of the other uses provided herein.

In some embodiments, the kit includes programming and/or software for executing any one or more of steps 10, 20, 30, 40, 50, 60, 70, 80, and/or 90 in FIG. 1B. In some embodiments, the programming and/or software is in a memory or on a computer readable memory. In some embodiments, the programming and/or software outputs the results of any of the processes in FIG. 1B. This can include outputting any correlation (or lack thereof) between the subject SNP signature and the sample SNP signature and/or the reference SNP signature to an end user, display, memory, and/or computer readable storage In some embodiments, the kit includes a SNP array and ingredients for running a SNP array. In some embodiments the kit includes tools for collecting a forensics sample. In some embodiments, the kits include PCR amplification ingredients. In some embodiments, the kit includes phi-29 and/or a similar polymerase. In some embodiments, the kits do not include all or any STR analysis ingredients.

Various Applications

In some embodiments, any of the methods described herein can be applied to determine if a subject's genetic material, such as DNA, matches, is consistent with, or is in a test genetic material sample. In some embodiments, one provides a likelihood that the subject's genetic material is within or the source of the genetic material in the test genetic material sample.

In some embodiments, any of the methods described herein can be applied to determine whether or not a subject is pregnant. In some embodiments, any of the methods described herein can be applied to determine if a male is the father of an unborn child. In some embodiments, the methods described herein can be applied to determine (including simply determining if the child's genetic material is consistent with) paternity or maternity of a child in comparison to one or more candidate parents. In some embodiments, any of the methods described herein can be applied to determine if there is an unknown person present in the test genetic material sample (in other words, if someone other than or in addition to the subject contributed to the test genetic material sample). In some embodiments, any of the methods described herein can be applied to determine if someone contributed to the test genetic material sample without having to assume or factor in the number of people that may have contributed to the test genetic material sample. In some embodiments, one performs the analysis of the test genetic material sample ignoring and/or without the knowledge and/or without estimating the number of individuals that contributed to a test genetic material sample. In some embodiments, any of the methods described herein can be applied to forensics. In some embodiments, any of the methods described herein can be applied to determine a percentage or a likelihood that the subject contributed genetic material (or the subject's genetic material is a match) to the test genetic material sample. In some embodiments, any of the methods described herein can be applied to determine or characterize the nature of various cells in a population of cells. This can be useful for sorting or selecting some cells over other cells, or determining the purity of a sample that comprises cells. In some embodiments, any of the methods described herein can be applied on various cells or tissue from a subject. For example, in some embodiments, one can use the methods on a sample from a biopsy and determine if there are malignant vs. benign cells, and/or healthy cells vs. cancerous cells, and/or the type of cancer present in the cells. In embodiments involving numerous cells types, in some embodiments, all or part of the cells can be examined together, instead of having to separate out individual cells. In some embodiments, any of the methods described herein can be applied to determine whether a test genetic material is from a human (and/or which human) in comparison to other nonhuman organisms.

In some embodiments, the subject SNP signature includes genetic material from (or data representing) multiple individuals. In some embodiments, this can allow for the comparison or screening of multiple individuals against a test genetic material. Thus in some embodiments, the subject SNP is actually one or more subjects to allow for screening one or more subjects against the test genetic material sample.

In some embodiments, the invention involves a method of identifying trace amounts of an individual's DNA within highly complex mixtures in forensic applications. Such applications include, for example, a situation in which the presence of DNA from numerous other individuals hampers the ability to identify the presence of any single individual. In some embodiments, any of the methods provided herein can be used to analyze genetic material that is degraded or from the mitochondria. The large number of assayed SNPs can allow the partitioning of sets of SNPs for different analyses, such that a small subset of SNPs becomes reserved for detecting these and other artifacts. In some embodiments, the test genetic material sample includes, or is assumed or believed to include genetic material from at least 2 subjects, for example, 2, 3, 4, 5, 6, 7, 8, 9, 10, 12, 14, 16, 18, 20, 25, 30, 40, 50, 60, 70, 80, 90, 100, 500, 1000, or more subjects, including any range defined between any two of the preceding values and any range above any one of the preceding values In some embodiments, one or more advantages of the invention include a focus on the ratio of intensity measures from common biallelic SNPs and more robust scaling in DNA quantity or quality at any given SNP. Additionally, in some embodiments, there is no need to assume a known number of individuals present in the mixture or have equal amounts of DNA from each individual present within the mixture. Furthermore, in some embodiments, it is easy to discern whether the mixture is closer to a population or towards the individual by utilizing a cumulative distance measure. Whereas few conclusions can be drawn by a SNP measurement that is slightly biased (less than 1%) towards an individual's genotype, considerable confidence can be gained by statistical analysis of the cumulative aggregate of all measurements across hundreds to millions of SNPs. In some embodiments 1,000-100,000 SNPs are used, including the range of 2,000 to 20,000, and 3,000 to 10,000 and approximately 5,000.

In some embodiments, using the genotypes of a given individual, it is possible to detect an individual's presence or absence in any study with available summary statistics.

SNP Signatures

As noted above, there are a variety of SNP signatures that can be useful in some or all of the disclosed embodiments. In some embodiments, each SNP signature comprises a collection of information about various SNPs (such as, for example, allele frequencies). In some embodiments, the SNP signature is a collection of SNP information regarding the subject, reference population, or test genetic material sample. In some embodiments, the information is expressed as a percentage. In some embodiments, the information is expressed in absolutes (e.g., presence or absence of a specific allele). In some embodiments, the SNP signature is expressed in terms of raw data that represents the alleles at the SNP. For example, in some embodiments, the SNP signature can be a fluorescence readout from a SNP array, which indicates which SNPs are present.

As will be appreciated by one of skill in the art, the size of a SNP signature (the number of SNPs that make it up) can vary based on how it is to be used. In some embodiments, where one is looking to see if an unknown person contributed to a test genetic material sample, relatively few SNPs are employed as any single unknown SNP present in the test genetic material sample can indicate the presence of an unknown person. In addition, in embodiments in which a lower number of people contributed (or may have contributed) to the genetic material in the test genetic material sample, fewer SNPs will be used than in situations in which a large number of people contributed to the TGMS (test genetic material sample).

In addition, the number of SNPs used in any one signature can also determine the degree of certainty that one has that the subject contributed to the TGMS. Thus, in embodiments, where a high degree of certainty is not required, fewer SNPs can be used. In embodiments where a higher degree of certainty is desired, more SNPs can be employed in the SNP signatures.

In some embodiments, there are enough SNP probes so that the degree of certainty that the person contributed to the test genetic material sample is 1 in at least any of the following: 1000, 10,000, 100,000, 1,000,000, 10,000,000, 100,000,000, 1,000,000,000, 5,000,000,000, or more.

In addition, in embodiments where one is only looking for the contribution of an unknown individual in a TGMS, as little as a single SNP can be used (assuming, for example, that none of the knowns have that specific SNP).

Thus, in some embodiments, as little as 1 SNP can be used, although many more can also be used. In some embodiments all of the SNPs in a subject are used. In some embodiments, all the SNPs across multiple subjects are used. In some embodiments, SNPs from various organisms or cells (such as various cancer cells) are used.

As will be appreciated by one of skill in the art, while the SNPs used in the various SNP signatures should overlap (that is the same SNPs should be in the sample SNP signature, the reference SNP signature and the subject's SNP signature), not all of the SNPs need to be present in all of the signatures. Thus, the number and identity of SNPs can be different across the different signatures. In some embodiments, the lowest number of SNPs is found in the subject's SNP signature.

In some embodiments, the SNP signature is at least one SNP. In some embodiments the SNP signature includes more than one SNP, for example 1, 5, 10, 15, 20, 100, 200, 300, 500, 1000, 2000, 3000, 5000, 9,000, 10,000, 15,000, 20,000, 30,000, 40,000, 50,000, 80,000, 90,000, 100,000 SNPs or more, including any amount defined between any two of the preceding values and any amount greater than any one of the preceding numbers.

A SNP signature can include one or more genotypes of one or more organisms (or cell types, etc.) across any number of individuals. As noted above, some SNP signatures include SNP information for 50,000 or more SNPs for tens, hundreds or more people. Other SNP signatures only include SNP information for a single person, across numerous SNPs, while yet other SNP signatures include SNP information for a single person and as little as a single SNP. Unless noted otherwise, any of the SNP signatures (sample SNP signature, reference SNP signature, subject's SNP signature) can vary in the manner noted above.

As noted above, the SNP signature does not have to be a compilation of mathematical values of the allele frequencies in all embodiments. For example, raw data showing intensity values for the various SNP probes (and thus representing what alleles are present) can be used. Similarly, the frequencies can be examined one at a time, and thus, a massive table of frequencies need not be compared to another massive table of frequencies. In some embodiments, the SNP signature merely represents or correlates to the allele information such that comparisons (mathematical, visual, or otherwise), can be consistently made between the subject and the sample and/or the reference population. Of course, in embodiments that do not employ SNPs, the consistency of the SNP is not relevant, but the consistency of the other item being monitored will be.

Analytical Methods and how SNP Signatures can be Compared

In some embodiments, the invention involves the use of any analytical methods that can be used to resolve complex mixtures. In some embodiments, the analytical method used can depend on the objective of the analysis. Non-limiting examples include an assumption that the SNPs on the array are independent from one another, an assumption that multiple SNPs on the arrays are correlated and are not independent (especially in the case of increasing microarray density). Further examples include using population databases such as from the HapMap Project to select a subset of independent markers to be used in the analysis, the use of haplotype-based methods or Linkage Disequilibrium (LD) methods to combine information from correlated SNPs, the use of a Bayesian method to select the most informative SNPs derived from a training dataset, and the use of explicit redundancy in correlated markers.

In some embodiments, any method that allows for using numerous (e.g., thousands of) low-information content markers to make a cumulative decision about whether a person is, or is not, (or an unknown person is) in a mixture can be employed. In some embodiments, one can use a likelihood approach, a Wilcoxan-sign rank, a least-squaresfit, a t-test, Pearson correlation, Spearman rank correlation and/or a test of proportions. In some embodiments, any method that allows for using hundreds to thousands of measurements of genetic variants can be employed for the methods described herein.

As will be appreciated by one of skill in the art, there are a variety of ways of comparing the SNP signatures. While SNP signatures are not required for all of the embodiments described herein, when they are used, they can be compared in a variety of ways. In some embodiments, any comparison, as long as it allows one to determine direction or bias of an allele count and/or frequency within the test genetic material sample relative to an allele count and/or frequency of the reference and an allele count and/or frequency in a subject, can be used. In some embodiments, any of the computational methods disclosed herein can be employed for this. In some embodiments, such as when the SNP signature is shown in terms of raw data or a data readout (such as a fluorescence readout on a SNP array), it can be possible to use the data regarding the SNPs itself in the comparisons. Thus, while allele frequencies expressed as percentages can be used in some embodiments, in some embodiments, the SNP data itself is used in the comparisons.

Some embodiments of the invention further encompasses software that implements any of the methods and/or steps and/or processes described herein. Pre-compiled UNIX binaries are available for a software implementation of some embodiments of the method and can be found in the attached electronic appendix and Appendix A. In some embodiments, the software can run its analysis using raw data from either Affymetrix or Illumina or by using genotype calls. In some embodiments, the software is also able to normalize the test statistic using the reference population and/or adjust the mean test statistic using a specified individual. In some embodiments, the user can restrict the SNPs considered to a subset of the total available SNPs. For raw input data one can match the distribution of signal intensities for each raw data file to that of the mixture input file (see platform specific analysis). In some embodiments, multiple test statistics and distance calculations are implemented including the noted test statistic, Pearson correlation, Spearman rank correlation and/or Wilcoxon sign test. In some embodiments, the software is configured to determine direction or bias of an allele count and/or frequency within the test genetic material sample relative to an allele count and/or frequency of the reference and an allele count and/or frequency in a subject.

Reference Populations and Reference Signatures
Ancestry and Reference Populations.

In some embodiments, one possible assumption of some of the embodiments described herein is that the reference population (and reference SNP signature) should either (a) accurately matched in terms of ancestral composition to the mixture and person of interest or (b) be limited to analysis of SNPs with minimal (or known) bias towards ancestry. In some embodiments, it is useful to recognize that any single SNP will have a small effect on the overall test-statistic. Moreover, it is realistic that ancestry of the reference population could be determined by analysis of a small subset of SNPs, followed by analysis of a person's contribution to the mixture with a separate set of SNPs (recognizing that nearly 500,000 SNPs are assayed).

In some embodiments, mismatching ancestry can be accounted for by normalizing the test-statistic using a second reference population matched to the individual of interest obtaining the normalized test-statistic $S(Y_i)$. If the reference population of the mixture is mismatched, the reference population of the individual of interest will nonetheless normalize the results. Unlike the reference population of the mixture, the individual of interest's reference population is matched to the individual of interest's ancestry or population substructure and thus serves as an anchor for the distribution of $T(Y_i)$. Thus one can compute a p-value for observing the result $Y_i$ or more extreme for individual $Y_i$, assuming the reference populations for both the mixture and individual of interest are inferred correctly. Additionally, in some embodiments, when matching a reference population to the individual of interest, one can choose the mean reference population test-statistic mean mean($T_{pop}$) as a close relative to normalize for interesting familial relationships or other considerations. one could also choose to estimate the subject's reference population test-statistic standard deviation sd($T_{pop}$) from a heterogeneous population to give a conservative overestimate of the true standard deviation of the test statistic $T(Y_i)$. In some embodiments, the reference population matched to the subject accounts for error in selecting the reference population of the mixture.

In some embodiments, the reference population is ascertained by using ancestral informative markers that are non-redundant with markers used for detecting if a person is in a mixture. In some embodiments, the reference population is ascertained by using multiple reference groups to ascertain a genetic distance. In some embodiments, the reference population is ascertained by adding individuals selected from a database of SNP calls for many individuals to effectively make a 'reference population' matched to ancestrally informative markers. In some embodiments, the reference population is obtained by collecting the SNPs of various suspects, which can optionally include the person of interest. In some embodiments, the reference population is obtained from an individual, such as a cancer patient or candidate that desires to see if she is pregnant. In some embodiments, the reference population is a family or part thereof. In some embodiments, the reference population has no bias. In some embodiments, the reference population has a minimal bias measured by a genetic distance, genomic control, and which can be obtained using a subset of the SNPs not utilized for resolving within the mixture and not in linkage disequilibrium with any SNPs used in the analysis. In some embodiments, the reference population has a bias, but it is a known bias.

In some embodiments, the reference population is generally matched to the mixture at the SNPs being interrogated. In some embodiments, one can minimize variability by only utilizing SNPs with small differences (such as measured by low Fst) between cohorts. In some embodiments, one can also use a subset of several thousand SNPs to determine and match the approximate make up of a reference by essentially selecting individuals who have the shortest genetic distance to the mixture. High-information content SNPs can be used because they will be sensitive to different ancestral populations. In some embodiments, these SNPs are independent of those SNPs used to identify a person, and thus could be restricted to one particular population. In some embodiments, multiple references can be used and built into an overall likelihood statistic where a posterior probability is calculated.

In some embodiments, a large number of SNPs can have a correlation between each other, forcing the distribution to deviate from a normal distribution. In some embodiments, one can sample the distribution by computationally adding individuals known not to be in the mixture to the dataset and determining where along the test-statistic they fall. In some embodiments, additional methods, such as using correction for these correlations, can also be used, such as linkage disequilibrium measurements as obtained through the HapMap project.

In some embodiments, the reference population comprises genetic material from one or more organisms, viruses, cell types, etc. For example, in some embodiments, the reference population can include 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 300, 400, 500, 600, 700, 800, 900, 1000, 2000, 3000, 4000, 5000, 6000, 7000, 8000, 9000, 10,000, 50,000, 100,000, 500,000, 1,000,000, 5,000,000, 10,000,000, 100,000,000, 1,000,000,000, 5,000,000,000 or more different sources of genetic material.

In some embodiments, more than one reference and/or reference population and/or reference population signature can be employed by extending to a multiple dimensional test-statistic or distance measure.

Computational Aspects

While the present disclosure outlines the various methods in terms of processes, one of skill in the art will appreciate that any and/or all of the process/steps disclosed herein can be performed on a device. In some embodiments, the device is a computer with relevant software to perform one or more of the processes outlined herein. In some embodiments, the steps and processes disclosed herein can be implemented using combinations of one or more computing devices, such as webservers or peer-to-peer clients. For example, the steps or processes can be performed on a single computing device, or, alternatively, a single step or process, such as 70 or combination of steps or processes, such as 10-90, 10-70, 20-70, 30-70, 40-70, 50-70, 60 & 70, 70 & 40, 70 & 60, and/or, 70 & 90 can be implemented on a computing device in communication with other computing devices that perform other steps or combinations of steps.

The systems, methods, and techniques described here can be implemented in computer hardware, firmware, software, or in combinations of them. A system embodying these techniques can include appropriate input and output components, a computer processor, and a computer program product tangibly embodied in a machine-readable storage component or medium for execution by a programmable processor. A process embodying these techniques can be performed by a programmable processor executing a program of instructions to perform desired functions by operating on input data and generating appropriate output. In some embodiments, the techniques can advantageously be implemented in one or more computer programs that are executable on a programmable system including at least one programmable processor coupled to receive data and instructions from, and to transmit data and instructions to, a data storage system, at least one input component, and at least one output component. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Storage components suitable for tangibly embodying computer program instructions and data include all forms of non-volatile memory, including by way of example semiconductor memory components, such as Erasable Programmable Read-Only Memory (EPROM), Electrically Erasable Programmable Read-Only Memory (EEPROM), and flash memory components; magnetic disks such as internal hard disks and removable disks; magneto-optical disks; and Compact Disc Read-Only Memory (CD-ROM disks). Any of the foregoing can be supplemented by, or incorporated in, specially-designed ASICs (application-specific integrated circuits).

In some embodiments, the entire process, from SNP analysis to final output of a likelihood that a subject's genetic material is in a test genetic material sample is automated and/or computerized. In some embodiments, any of the results from steps 10-90 are output to an end user and/or a memory. In some embodiments, any 1, 2, 3, 4, 5, 6, 7, 8 or 9 processes outlined in FIG. 1B are performed and/or output via a computer. In some embodiments, a computer prepares one or more SNP signatures and a person can make the comparison between the SNP signatures. In some embodiments, a first computer can prepare one or more of the SNP signatures, a second computer can prepare a different SNP signature, and a third computer can compare the different SNP signatures. In some embodiments, the SNP signatures are standardized and contained in a memory system, cd, dvd, or other storage device. In some embodiments, such stored or standardized SNP signatures are for reference SNP signatures, subject SNP signatures, and/or sample SNP signatures. In some embodiments, the software and/or hardware is configured to detect various markers of various SNPs, develop the various SNP signatures (e.g., subject's SNP signature, test genetic material SNP signature and reference population SNP signature) and compare the SNP signatures.

In some embodiments, programming is provided that allows for the analysis of a SNP array. In some embodiments the analysis comprises data regarding fluorescence at various locations on the array of fluorescence generally. In some embodiments, the programming allows for the comparison of a first SNP array (such as a subject SNP signature array) with a) second SNP array (such as a reference SNP signature array) and/or b) a third SNP array (such as a sample SNP signature array).

In some embodiments, one or more of the steps in FIG. 1B are performed by different users and/or devices. In some embodiments, the computer, device, memory, etc., comprises programming to allow for direction or bias of an allele count or frequency within a mixture relative to a reference and an in individual of interest to be determined. In some embodiments, the computer, device, memory, etc., employs one or more of the formulas provided herein.

In some embodiments, the systems and methods described herein can advantageously be implemented using computer software, hardware, firmware, or any combination of software, hardware, and firmware. In one embodiment, the system is implemented as a number of software modules that comprise computer executable code for performing the functions described herein. In certain embodiments, the computer-executable code is executed on one or more general purpose computers. However, a skilled artisan will appreciate, in light of this disclosure, that any module that can be implemented using software to be executed on a general purpose computer can also be implemented using a different combination of hardware, software or firmware. For example, such a module can be implemented completely in hardware using a combination of integrated circuits. Alternatively or additionally, such a module can be implemented completely or partially using specialized computers designed to perform the particular functions described herein rather than by general purpose computers.

Some embodiments of the invention are described with reference to methods, apparatus (systems) and computer program products that can be implemented by computer program instructions. These computer program instructions can be provided to a processor of a general purpose computer, special purpose computer, or other programmable data processing apparatus to produce a machine, such that the instructions, which execute via the processor of the computer or other programmable data processing apparatus, create means for implementing the acts specified herein to transform data from a first state to a second state.

These computer program instructions can be stored in a computer-readable memory that can direct a computer or other programmable data processing apparatus to operate in a particular manner, such that the instructions stored in the computer-readable memory produce an article of manufacture including instruction means which implement the acts specified herein.

The computer program instructions can also be loaded onto a computer or other programmable data processing apparatus to cause a series of operational steps to be performed on the computer or other programmable apparatus to produce a computer implemented process such that the instructions that execute on the computer or other programmable apparatus provide steps for implementing the acts specified herein.

In some embodiments, the invention further encompasses the use of a library of $Y_i$ arithmetic means derived from AA, AB, and BB to map genotype calls to expected $Y_i$ values to each SNP from individually genotyped samples.

As noted herein high-density SNP genotyping data was used to resolve complex mixtures. In one embodiment, the method comprises the construction of a series of simulations to evaluate the theoretical limits of resolving an individual within a mixture using the described analytical framework and given characteristics of current generation SNP genotyping microarrays. In some embodiments, the method further comprises experimentally testing the feasibility of detecting if an individual is contributing trace amounts of DNA to highly complex mixtures. Within these simulations and experimental tests, particular focus was given (for some of the embodiments) on complex mixtures—those containing hundreds or thousands of individuals. Such approaches have utility in resolving a mixture of DNA from common surfaces where many individuals have left DNA.

As demonstrated through proof of principle experiments below, to resolve mixtures where the person of interest is less than 1% of the total mixture, conservatively 25,000 SNPs can be sufficient to achieve a p-value of less than $10^{-6}$. If one were to use all the available SNPs, one can easily resolve mixtures where the person of interest is less than 0.1% of the total mixture to achieve a p-value of less than $10^{-6}$.

In some embodiments, the invention involves a cumulative analysis of shifts in allele probe intensities in the direction of the individual's genotype. In some embodiments, the invention involves a method of measuring the difference between the distance of the individual from a reference population and the distance of an individual from the mixture. In some embodiments, one advantage the invention holds over other methods in field is that the method does not require knowledge of the number of individuals in the mixture and is capable of discriminating an individual source from a mixture comprising over one thousand sources.

The above discussion and Example 1 provides an explanation of some of the embodiments with modifications in response to various factors including homogeneity of the mixture and accuracy of the reference populations.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

Example 1

Complex Mixture Constructions.

A total of 8 complex mixtures were constructed (See Table 1). Concentrations of all DNA samples were checked in triplicates using the Quant-iT PicoGreen dsDNA Assay Kit by Invitrogen (Carlsbad, Calif.). An eight point standard curve was prepared using Human Genomic DNA from Roche Diagnostics (Cat #: 11691112001, Indianapolis, Ind.). The median concentrations were calculated for each individual DNA sample.

TABLE 1

| Name | Description | Illumina 550K | Illumina 450S | Affymetrix 5.0 |
| --- | --- | --- | --- | --- |
| Mixture A | Equimolar pool. Equimolar mixture of 41 CEU individuals (14 Trios minus one individual) | Yes | No | Yes |
| Mixture B | Equimolar pool. Equimolar mixture of 47 CEU individuals (16 Trios minus one individual) | Yes | No | Yes |
| Mixture C | 2-person mixture. 90% one CEU individual, 10% a second CEU individual | Yes | No | Yes |
| Mixture D | 2-person mixture. 99% one CEU individual, 1% a second CEU individual | Yes | No | Yes |
| Mixture E | Complex mixture. Mixture with 184 individuals at ~0.2% each, and 41 individuals from Mixture A at ~1% each. | Yes | No | No |
| Mixture F | Complex mixture. Mixture with 184 individuals at ~0.2% each, and 47 individuals from Mixture B at ~1% each. | Yes | No | Yes |
| Mixture G | Complex mixture. Mixture with 184 individuals at ~0.2% each, and 41 individuals from Mixture B at ~0.1% each. | No | Yes | No |
| Mixture H | Complex mixture. Mixture with 184 individuals at ~0.5% each, and 47 individuals from Mixture B at ~0.1% each. | No | Yes | No |

Mixtures A1, A2, B1, and B2: Equimolar mixtures of HapMap individuals.

Shown in Table 1, two main mixtures (mixtures A and B) were composed in duplicates resulting in a total of 4 mixtures. Mixture A was composed of 41 HapMap CEU individuals (14 trios minus one individual) and mixture B was composed of 47 HapMap CEU individuals (16 trios minus one individual).

Mixture C1: 90% NA12752 and 10% NA07048.

Two CEU males were combined in a single mixture so that one individual (NA12752) contributed 90% (675 ng) of the DNA in the mixture, while the other individual (NA07048) contributed 10% (75 ng) DNA into the mixture by concentration.

Mixture C2: 90% NA10839 and 10% NA07048.

Two CEU individuals, a female and a male, were combined in a single mixture so that one individual (NA10839)

contributed 90% (675 ng) of the DNA in the mixture, while the other individual (NA07048) contributed 10% (75 ng) DNA into the mixture by concentration.

Mixture D1: 99% NA12752 and 1% NA07048.

Two CEU males were combined in a single mixture so that one individual (NA12752) contributed 99% (742.5 ng) of the DNA in the mixture, while the other individual (NA07048) contributed 1% (7.5 ng) DNA into the mixture by concentration.

Mixture D2: 99% NA10839 and 1% NA7048.

Two CEU individuals, a female and a male, were combined in a single mixture so that one individual (NA10839) contributed 99% (742.5 ng) of the DNA in the mixture, while the other individual (NA07048) contributed 1% (7.5 ng) DNA into the mixture by concentration.

Mixture E: 50% Mixture A1 and 50% Mixture of 184 equimolar Caucasians.

Two mixtures were combined into a single mixture so that each of the original mixtures contributed the same amount of genomic DNA by volume into the final mixture. CAU2 mixture contained 184 Caucasian control individuals obtained from the Coriell Cell Repository. Mixture A1 was constructed as above and contained 41 CEU individuals.

Mixture F: 50% Mixture B2 and 50% Mixture of 184 equimolar Caucasians.

Two mixtures were combined into a single mixture so that each mixture contributed the same amount of genomic DNA by volume into the final mixture. CAU3 mixture contained 184 Caucasian control individuals obtained from the Coriell Cell Repository. Mixture B2 was constructed as above.

Mixture G: 5% Mixture A2 and 95% Mixture of 184 equimolar Caucasians.

Two mixtures were combined into a single mixture with Mixture A2 comprising of 5% of the mixture and the CAU3 comprising of 95% of the mixture. CAU3 mixture contained 184 Caucasian control individuals obtained from the Coriell Cell Repository. Mixture A2 was constructed as above.

Mixture H: 5% Mixture B1 and 95% Mixture of 184 equimolar Caucasians.

Two mixtures were combined into a single mixture with Mixture B1 comprising of 5% of the mixture and the CAU2 comprising of 95% of the mixture. CAU2 mixture contained 184 Caucasian control individuals obtained from the Coriell Cell Repository. Mixture B1 was constructed as above.

Genotyping.

Four cohorts were assayed on the Illumina (San Diego, Calif.) HumanHap550 Genotyping BeadChip v3, one cohort was assayed on the Illumina (San Diego) HumanHap450S Duo, and three cohorts were assayed on the Affymetrix (Emeryville, Calif.) Genome-Wide Human SNP 5.0 array, with each cohort being assayed on a single chip. Probe intensity values were extracted for analysis from the file folders generated by the BeadScan software for the Illumina platform, and from Affymetrix GTYPE 4.008 software for the Affymetrix data, as described in previous studies (See Pearson, J. V. et al. Identification of the genetic basis for complex disorders by use of pooling-based genomewide single-nucleotide-polymorphism association studies. *Am J Hum Genet* 80, 126-139 (2007)).

Platform Specific Analysis.

With the Affymetrix platform the genotypes were used for each individual and found similar results with the Illumina platform. Additionally, the raw CEL files were used from the HapMap dataset (See The International HapMap Project. *Nature* 426, 789-796 (2003)) found at the world wide web at HapMap.org. To overcome the differences in distribution of signal intensity between CEL files, the distribution of the signal intensities were matched to the distribution of the mixture's CEL file. This was achieved by ordering allele frequencies on a given chip (and allele frequencies in the mixture). The $i^{th}$ allele frequencies from the mixture of interest were substituted for the $i^{th}$ allele frequencies of the given chip. Without this adjustment, there was difficulty resolving any individual in any mixture due to the fact that off-target cross-hybridization was not accounted for. In some embodiments, this type of adjustment is the preferred type of normalization method when raw data is available for the mixture, person of interest, and reference population.

With the Illumina platform the genotypes from the HapMap dataset (See The International HapMap Project. *Nature* 426, 789-796 (2003)) were used of both the person of interest and the reference populations instead of raw intensity values as had been done with the Affymetrix platform. With the mixture the raw intensity values were used. This set of data mimics the case where raw data may not be available but genotype calls are available. Reduction in errors between different microarrays was achieved by normalizing each microarray by dividing by the mean channel intensity from each respective channel. This was performed on the raw data from the mixture. This platform specific adjustment may not be needed when the raw data of a person's genotype is present on the same platform. In the Illumina specific example, the calls from the HapMap were utilized without having platform specific genotype data.

Simulation.

Simulation was used to test the efficacy of using high-density SNP genotyping data in resolving mixtures. The relevant variables of the simulation are: the number of SNPs s, the fraction f of the total DNA mixture contributed by the person of interest $Y_i$, and the variance or noise inherent to assay probes $v_p$. In the simulations, theoretical mixtures were composed by randomly sampling individuals from the 58C Wellcome Trust Case-Control Consortium (WTCCC) dataset (See Genome-wide association study of 14,000 cases of seven common diseases and 3,000 shared controls. *Nature* 447, 661-678 (2007)). After removing duplicates, relatives and other data anomalies, a total of 1423 individuals remained. The genotype calls for these individuals were provided from the WTCCC and were previously genotyped on the Affymetrix 500K platform. Within each simulation, N individuals were randomly chosen to be equally represented in the mixture and then computed the mean allele frequency ($Y_i$) of the mixture for each SNP. SNPs j with an observed $Y_{ij}$ below 0.05 or above 0.95 in the reference population were removed due to their potential for having false positives and low inherent information content.

A microarray was simulated that would contain a mean of 16 probes for simplicity, approximating the mean number of probes found on the Illumina 550K, Illumina 450S Duo and Affymetrix 5.0 platforms (18.5, 14.5 and 4 respectively). For each SNP j the $Y_{ij}$ of each probe was added to a Gaussian noise based off the previously measured probe variance. When fixed, probe variance was set to 0.006 when simulating Affymetrix 5.0 arrays, and to 0.001 for both Illumina 550K and Illumina 450S Duo arrays. The allele frequency of the mixture was then calculated to be the mean of these probe values. A mixture size of N is equivalent to saying that an individual's DNA represents $f=1/N^{th}$ of the total DNA in the mixture. Equimolar mixtures ranging from 10 individuals to 1,000 individuals were tested. Using this design, each individual was tested for their presence where they contributed between 10% and 0.1% genomic DNA to the total mixture. To obtain significance levels (p-values) to test the null hypothesis, the normal distribution was sampled. There were not enough samples to test the tail of the distribution and therefore the p-values are not completely accurate (e.g. below $10^{-6}$). Nonetheless, p-values are expected to be sufficiently accurate to qualitatively assess the limits of the method.

Joint Adjustment of Mixture Fraction (f) and Number of SNPs (s).

The trade-off between the numbers of SNPs considered versus the fraction of the DNA mixture belonging to the person of interest were tested. One expects greater ability to resolve individuals from a mixture when more SNPs are used in the calculation, though the absolute limits of detection are ultimately determined by the genetic variation of the population. A variance ($v_p$) was assumed for the estimated allele frequency of each probe of 0.001, which follows closely the observed variance (0.00158) of the Illumina 550K platform across multiple arrays in other genotyping studies. FIG. 2a shows 10,000 simulations ranging from s=10 to s=500,000 and f=0.1 to f=0.001, where the Z-axis is the p-value. With 10,000 to 25,000 SNPs it was possible to resolve mixtures where the person of interest was less than 1% of the total mixture at a p-value of less than $10^{-6}$. The shading on the pvalues for FIG. 2a is noted in the bar beneath the graph. Dark grey is present primarily on the lower and left-hand side, followed by a band of white (as one moves upward and to the right), followed by an area of grey.

Joint Adjustment of Probe Variance ($v_p$) and Mixture Fraction (f).

In these simulations, it was assumed that there were 50,000 SNPs on each microarray (s=50,000). While conceivably a much greater number of SNPs could be used, the lower number of SNPs would be more realistic in a setting where preference has been given to SNPs whose allele frequencies minimally vary across different populations. FIG. 2b shows 10,000 simulations from $v_p$=0.0001 to $v_p$=0.01 and f=0.1 to f=0.001. It is clear that within a small amount of probe variance one is able resolve an individual who comprises of one-thousandth of a mixture. If the probe variance is below 0.001 one can easily resolve an individual whose DNA comprises 10% to 0.1% of the mixture. Even with increasing noise, one is still able to resolve mixtures where the person of interest contributes less than 2.5% with a p-value of less than $10^{-6}$. One can also observe that the probe variance does not have a large impact on the p-value, and in this case the fraction of the mixture is the important factor when the number of SNPs is fixed. The shading on the pvalues for FIG. 2b is noted in the bar beneath the graph. Dark grey is present primarily on the lower and right-hand side, followed by a band of white (as on moves left and upward across the graph), followed by an area of grey.

Joint Adjustment of Number of SNPs (s) and Probe Variance ($v_p$).

Finally the trade-off between the number of SNPs and the probe variance was examined. It was assumed that the person of interest contributes 1% to the mixture (f=0.01). FIG. 2c shows 10,000 simulations from s=10 to s=500,000 and $v_p$=0.0001 to $v_p$=0.01. The probe variance has little effect on the significance of the test. Consequently, it would be sufficient to use 50,000 SNPs, even with very high levels of noise to resolve mixtures of sizes up to 100. Within simulations, the number of probes is fixed to be 16, and thus the noise does not affect the allele frequency estimate, as would be the case with arrays using 4 probes. The shading on the pvalues for FIG. 2c is noted in the bar beneath the graph. Dark grey is present primarily on the left-hand side, followed by a band of white (as one moves to the right), followed by an area of grey.

Equimolar Mixtures Versus Two Person Mixtures.

The same three simulation designs were performed using mixtures that included two individuals. Instead of N=1/f individuals contributing equally to the mixture, mixtures were created where individual one would make up (N−1)/N of the mixture and individual two would make up 1/N of the mixture. When the three simulations were performed an increase in significance (smaller p-values) was observed. This gives further utility to the method when there are a small number of total contributors with the person of interest making up a small fraction of the mixture.

Conclusions from Simulations.

Herein it was demonstrated that 10,000 to 50,000 SNPs to resolve mixtures where the genomic DNA of the person of interest composes 10% to 0.1% of the DNA within the total mixture. Perhaps counter intuitively, noise plays an important but secondary role since microarray technologies such as the Illumina 550K and Illumina 450S Duo platforms have a sufficiently large number of replicate probes compared to population sampling variance. Another consideration is that the choice of SNPs was not made with any specific intent and therefore one could reduce the number of SNPs significantly if one choose the most informative SNPs, for example by choosing a set of SNPs that do not vary across differing populations.

Experimental Validation

To examine empirically the efficacy of the above noted method various known mixtures were formed of DNA from HapMap individuals and genotyped the mixtures on three different platforms. Listed in Table 1 and detailed herein are the compositions of the different mixtures formed and the platforms they were assayed across. The use of mixtures of HapMap individuals has several advantages. First, one can be confident of the genotype calls because in most cases more than one platform has been used to identify the consensus genotype. Second, trios are available, which allow the evaluation of identifying an individual using a relative's genotype data. Third, by using mixtures of multiple HapMap individuals one can evaluate the ability to resolve each individual within the mixture. Therefore simple two-person mixtures were constructed as well as complex mixtures containing contributions from 40+ individuals. With each mixture, the HapMap CEU individuals not present in the mixture were used as the reference population of the mixture.

Resolving an Individual within Mixtures of 40+ Individuals.

FIG. 3 shows the test-statistic for each individual within each mixture. Both individuals in the mixture and not in the mixture were tested for presence within the mixture. On each graph, the left y-axis represents the −log p-value, the right y-axis represents the normalized test-statistic $S(Y_{i,j})$, and the bottom axis represents each individual. Each experiment was performed more than once and thus there are multiples of 86 individuals indexed on the bottom axis. For mixtures A, B, E, F, G and H, those in the mixture are shaded lightly and identified and those not in the mixture are shaded darker and identified. All individuals in the mixtures composed of more than 40 individuals were identified with zero false positives Resolving Members within 2 Person Mixtures (f=1% and f=10%).

For mixtures C and D, those individuals who are not in the mixtures are shaded dark and identified, those individuals who are related to a person in the mixture are colored orange, and those people in the mixture are shaded lighter and identified. It was possible to correctly identify individuals within the mixture with zero false-positives except, as expected, for relatives of individuals in the mixture, which appear at a midpoint between those in and those not in the mixture.

Resolving an Individual from a Mixture Using a Relative's Genotypes.

It is interesting to observe that there were no false-positives in the Mixture A, B, E, F, G or H but there were false-positives when considering Mixture C and D. This is not unexpected since the HapMap CEU population is composed of trios and one is in fact resolving that the mother or father of the individual (a son or daughter) is in the mixture; data point indicated as "1-10" and "90-99" marked individuals being observed as significant in FIGS. 3a and 3c. Thus, one can easily resolve an individual (son or daughter) even when using their mother's genotypes or father's genotypes.

Resolving an Individual from a Mixture with 50,000 SNPs.

In FIG. 3a, one can observe that all the mixtures are able to be resolved with no false-negatives when one uses all 504,605 SNPs present on the Illumina 550K platform. The same analysis was performed considering 50,000 SNPs (see FIG. 3b) and found that the samples had the same degree of separation. Thus, even if a small fraction of the intended genotypes are generated (such as in a degraded sample), identification of an individual in a complex mixture is possible.

Resolving an Individual when Contributing Less than 1%.

In FIG. 3d, mixtures G and H were considered where the fraction of DNA of each individual is between 0.15% and 0.25% of the total mixture. One can see that using all the SNPs available one was able to resolve all the mixtures with no false-negatives on the Illumina 450S Duo platform. One can therefore resolve an individual even when the fraction of their DNA in the mixture is less than 1%.

Example 2

This example demonstrates a method to detect the presence of an individual's genetic material (nucleic acid) in a complex mixture of genetic material from multiple subjects.

First, a reference sample of genetic material is created to provide an estimate of the mean allele frequencies of SNPs in the population represented by the reference sample (to obtain a reference SNP signature). The reference sample can be constructed by obtaining samples of genetic material from a commercial provider, such as the Coriel Cell Repository (Coriel Institute for Medical Research, Camden, N.J.). The reference sample is composed of genetic material from one hundred individuals of Caucasian descent. The genetic material for the reference sample is available from the Coriel Cell Repository, Catalog number HD100CAU.

Next, the specific SNPs to be included in the analysis are selected. The allele frequencies of all selected SNPs in the reference sample are measured. Once measured, SNPs with a mean allele frequency less than 0.05 or greater than 0.95 are eliminated from consideration. All remaining SNPs are selected for use in the subsequent analysis, and the mean allele frequencies from those remaining SNPs are recorded. Alternatively, the allele frequencies of the selected SNPs can be obtained from a database that has previously measured the allele frequencies of the selected SNPs in a comparable reference population.

Next, a complex mixture that contains DNA from numerous sources is collected and the mean allele frequencies of the SNPs selected above are then determined for the complex mixture.

Next, a sufficient amount of DNA is taken from a person of interest (or subject). This DNA is analyzed to determine the allele frequencies of the selected SNPs in the DNA from the person of interest.

Finally, the data obtained from the SNPs of the person of interest is compared with the data obtained from the reference sample and the data from the mixture to determine the source of the unknown sample. This process is repeated for a sufficient number of the selected SNPs to obtain the degree of certainty desired for establishing the match of the person of interest's DNA to the DNA in the complex mixture. The results from each SNP are combined and the output indicates the likelihood that the genetic material in the complex mixture belongs to the individual of interest.

Example 3

In this example, the methods in the current disclosure are used for a forensic application. First, a reference sample of genetic material is assembled to provide an estimate of the mean allele frequencies of the SNPs to be analyzed in a given human population. The reference sample is constructed by obtaining samples of human genetic material from a commercial provider such as the Coriel Cell Repository (Coriel Institute for Medical Research, Camden, N.J.). Genetic material from various human populations is available from the Coriel Cell Repository, including panels of individuals of Caucasian, African American, Middle Eastern, Asian, and other ethnic descents. In this example, reference samples representing panels of 10 or more individuals of Caucasian, African American, Middle Eastern, and Asian descent are obtained from the Coriel Cell Repository and combined to form the reference sample. The reference sample is then tested to determine the mean allele frequencies of all available SNPs and create a reference SNP signature. Alternatively, the mean allele frequencies of the SNPs to be analyzed can be obtained from a commercial database (thereby obtaining the reference SNP signature). SNPs returning a frequency value below 0.05 or above 0.95 can optionally be eliminated from consideration.

Next, a subject SNP signature is created by obtaining genetic material from the individual who is suspected of contributing genetic material to a sample obtained at a crime scene. The allele frequencies of the selected SNPs are measured for a genetic material sample from the subject to obtain the subject SNP signature.

Next, the sample of genetic material from the crime scene (test genetic material sample) is analyzed. The test genetic material sample is analyzed and the mean allele frequencies of the selected SNPs are obtained and recorded, thereby providing the sample SNP signature.

Finally, each of the signatures is compared to determine whether the unknown sample taken from the crime scene belongs to the subject. The subject SNP signature (e.g., the allele frequency of each SNP for the subject) is compared to the reference SNP signature (e.g., the mean allele frequency of the same SNP in the reference) and compared to the sample SNP signature (the mean allele frequency in the test genetic material sample).

The output can be expressed in terms of the likelihood that the subject contributed to the test genetic material sample.

Example 4

In this example, the methods in the current disclosure are used to conduct a forensic analysis of a sample that has been degraded as a result of exposure to environmental or other factors.

A reference sample of genetic material is assembled to provide an estimate of the mean allele frequencies of the SNPs to be analyzed in a given human population, and thereby provide a reference SNP signature. Genetic material from various human populations is available from the Coriel Cell Repository, including panels of individuals of Caucasian, African American, Middle Eastern, Asian, and other ethnic descents. Genetic material samples representing panels of 10 or more individuals of Caucasian, African American, Middle Eastern, and Asian descent are obtained from the Coriel Cell Repository and combined to form the reference sample. The reference sample is then tested to determine the allele frequencies of all available SNPs, thereby creating a reference SNP signature. Optionally, SNPs returning a frequency value below 0.05 or above 0.95 are eliminated from consideration.

A subject's genetic material is then collected from one or more individuals that are suspected of contributing genetic material to a test genetic material sample. In this example, genetic material is collected from 10 different suspects who had access to the location of the test genetic material sample. The genetic material from all 10 individuals is combined to form a mixture sample, and the allele frequencies of the selected SNPs are measured, thereby forming a subject SNP signature.

Next, the degraded sample of genetic material is analyzed. The allele frequencies of the selected SNPs are measured and recorded, creating a sample SNP signature.

Finally, the signatures (or at least a part thereof) obtained from each sample are compared to determine whether the degraded sample belongs to one of the 10 individuals who contributed genetic material to the test genetic material sample. The allele frequency of at least some of the SNPs in the degraded sample is compared to the mean allele frequency of the same SNPs in both the reference sample and the mixture sample. This process is repeated as many times as necessary for the selected SNPs. One thereby obtains enough SNP comparisons to determine if one of the 10 subjects contributed to the genetic material in the test genetic material sample.

Example 5

In this example, the methods of the current disclosure are used to determine whether a human female is pregnant.

First, a suitable sample (a sample that can contain genetic material from a fetus in the host) is taken from the female host for analysis. The genetic material in the sample is isolated and a sample SNP signature is prepared from the genetic material. A subject SNP signature is then prepared by using a sample from the female subject.

The sample SNP signature is compared to the subject SNP signature, and if the comparison reveals that another person's genetic material is present, such as through additional SNPs, one concludes that the host is pregnant.

In the alternative, a further reference SNP signature can be used from an appropriate reference population, and the comparison can be between a) the subject SNP signature and each of b) the reference SNP signature and the sample SNP signature.

Example 6

In this example, the methods of the current disclosure are used to determine the paternity of an unborn child.

First, a suitable sample is taken from a pregnant female for analysis. The sample will include genetic material from the unborn child. The SNPs in the sample are determined and a sample SNP signature is obtained from the unborn child. The sample can optionally include the mother's genetic material.

Next, a suitable sample is obtained from the potential father and a SNP signature is prepared for the potential father.

The SNP signature of the potential father can be compared to the sample SNP signature, and when the sample SNP signature only includes genetic material from the child, the likelihood that the potential father is the father of the child can be determined.

In the alternative, a reference SNP signature can be prepared and the SNP signature of the potential father can be compared to each of the reference SNP signature and the sample SNP signature to determine if the potential father contributed to DNA of the unborn child.

As will be appreciated by one of skill in the art, one is not looking for specific matches between the SNPs in the sample SNP signature and the SNP signature of the potential father, but rather a degree of similarity that is consistent with paternity.

Example 7

In this example, a method is used to determine whether unknown tissue remains are of bovine or human origin. First, a reference sample is created by obtaining a sample of bovine genetic material. The bovine genetic material can be obtained from a donor bovine animal, or can be obtained from a commercial provider, such as the Coriel Cell Repository. The sample of bovine genetic material is prepared and analyzed to determine the mean allele frequencies of 1,000 SNPs. Remaining SNPs are selected for analysis and their values are recorded.

Next, a sample of human genetic material is prepared. The human genetic material can be obtained from a human donor, or can be obtained from a commercial provider, such as the Coriel Cell Repository. The human genetic material is analyzed, using the methods in the current disclosure, to determine the mean allele frequencies of the selected SNPs. Once obtained, the values are recorded.

Next, a sample of genetic material is prepared from the unknown tissue remains. The unknown sample is analyzed and the mean allele frequencies of the selected SNPs are obtained and recorded.

Finally, the data obtained from each sample are compared to determine the source of the unknown sample. The mean allele frequency of each SNP in the unknown tissue remains sample is compared to the mean allele frequency of the same SNPs in each of the bovine sample and the human sample. If the SNP frequencies of the unknown sample are more similar to the bovine allele frequencies, it will indicate a lower chance that the sample is human and if the SNP frequencies of the unknown sample are more similar to the human allele frequencies, it will indicate a lower chance that the sample is bovine. The results from each SNP are combined and summed, and the output indicates whether the unknown tissue remains are of bovine or human origin.

Example 8

Many cell lines are most successfully cultured by growing the cells of interest along with supporting cell types.

Examples include culturing human embryonic stem cells on a layer of mouse embryonic feeder cells, or growing primary human hepatocytes in co-culture with rat microvascular endothelial cells. In some embodiments, the methods in the current disclosure provide a quick and accurate method for distinguishing between cells of interest and supporting cells.

In this example, an embryonic stem cell line is cultured in co-culture with several different mouse embryonic feeder cells for several passages. After culturing the embryonic stem cells for several passages, the embryonic stem cells are isolated from the mouse embryonic feeder cells. The methods of the current disclosure are then used as described below.

First, a reference sample is created by combining genetic material from the several different feeder cell lines that are used to culture the embryonic stem cell line of interest. The mean allele frequencies of numerous available SNPs in the reference sample are measured and the values are recorded.

Next, a sample of genetic material is obtained from the cell line of interest. In this example, the cell line of interest is a human embryonic stem cell line that is available from the NIH. A sample of this cell line is obtained, and the allele frequencies of the selected SNPs are measured and recorded.

After being successfully cultured for one or more passages in a co-culture with the three different types of feeder cells, the embryonic stem cells of interest are isolated from the feeder cells. To confirm that the embryonic stem cells have been successfully isolated from the feeder cells, a sample of isolated embryonic stem cells is collected and the genetic material from the cells is prepared for analysis. The mean allele frequencies of the selected SNPs in the sample are obtained and recorded.

Finally, the data obtained from the sample of isolated embryonic stem cells are compared to the data obtained from each of the embryonic stem cell sample and the feeder cell mixture sample. The allele frequency of each SNP in the isolated embryonic stem cell sample is compared to the mean allele frequency of the same SNP in each of the embryonic stem cell sample and feeder cell mixture sample. This process is repeated for all of the selected SNPs. The results from each SNP are combined and the output indicates whether the isolated embryonic stem cell sample is free of feeder cells.

Example 9

When a biopsy is performed on a tumor, cells from the tumor are typically analyzed to determine whether the cells are malignant or benign. The methods in the current disclosure can be used to analyze cells from a tumor biopsy and determine whether those cells are malignant or benign.

First, a benign tumor sample is created by combining genetic material from several different known benign tumor cells and/or healthy cells. In this example, several different known forms of benign bone tumors are used to create the sample. The mean allele frequencies of all available SNPs in the benign tumor sample are measured and the values are recorded.

Next, a malignant tumor sample is created to represent the different types of malignant bone cancers. In this example, several different known forms of malignant bone tumors are used to create the sample. Genetic material from malignant tumors classified as multiple myeloma, osteosarcoma, Ewing's sarcoma, and chondrosarcoma are combined to create the malignant tumor sample. The mean allele frequencies of the selected SNPs in the malignant tumor sample are measured and the values are recorded.

Next, a tissue biopsy is obtained from an unknown bone tumor and cells are isolated from the biopsied tissue using methods that are well known in the art. The genetic material from the cells is isolated and the mean allele frequencies of the selected SNPs are measured and recorded.

Finally, the data obtained from the tumor biopsy sample are compared to the data obtained from each of the benign tumor sample and the malignant tumor sample. The mean allele frequency of each SNP in the unknown tumor biopsy sample is compared to the mean allele frequency of the same SNP in each of the benign tumor sample and the malignant tumor sample. This process is repeated for a sufficient number of the selected SNPs. The results from each SNP are combined, and the output indicates whether the tumor is composed of benign or malignant cells.

Example 10

This example demonstrates one method of comparing allele frequencies for a SNP. A first set of SNP data are identified as the reference population, and a second set of SNP data are identified as the mixture population. For each individual SNP, the allele frequency values of the data in the reference population are averaged to provide a mean allele frequency value for each SNP in the reference population (thereby providing a reference SNP signature). This process is repeated with the mixture population, providing a mean allele frequency value for each SNP in the mixture population (thereby providing a sample SNP signature).

For any given subject's SNP, the value of the allele frequency at each subject's SNP is compared to the mean allele frequency value of the same SNP in both the reference population and the sample SNPs from the mixture.

For the first SNP to be analyzed, the mean allele frequency of the SNP in the mixture is subtracted from the SNP allele frequency value of the subject, and the absolute value of this difference is stored. Next, the mean allele frequency of the SNP in the reference population is subtracted from the SNP allele frequency value of the subject, and the absolute value of this difference is stored. Finally, a value is obtained for the individual SNP by subtracting the absolute value of the first value from the second value.

A negative value (down to −0.5) denotes that the subject is likely to be in the reference population. A positive value (up to 0.5) denotes that the subject is likely to be in the mixture, and a value of 0 denotes that the subject is equally likely to be in the mixture and the reference population.

In some embodiments, the above process can be repeated across all SNPs to be included in the analysis, and the value $Y_{i,j}$ obtained for each SNP is summed as follows:

$$D(Y_{i,j}) = |Y_{i,j} - \text{Pop}_j| - |Y_{i,j} - M_j| \qquad \text{(Equation 1)}.$$

The summation result is used to determine whether the subject is a member of the mixture population, a member of the reference population, or neither. Additionally, a one-sample t-test for individual i can be taken and used to obtain a test statistic as follows:

$$T(Y_i) = (\text{mean}(D(Y_{i,j})) - \mu_0)/(sd(D(Y_{i,j})/\text{sqrt}(s))) \qquad \text{(Equation 2)}$$

One can use multiple references, extending this formula to a multi-dimensional test statistic. This may be especially useful for a person of mixed ethnicity, though no not necessary.

Example 11

Different populations will have different mean SNP allele frequencies based on the genetic heritage of the population.

This example provides one method of constructing a reference population for use with the methods of the current disclosure. Such a reference population can be used to manage the effect of ancestry on the allele frequencies observed across many samples.

First, the subject's population is identified. If the subject is of Caucasian ancestry, a reference sample is created based on a Caucasian population. The reference sample can typically include samples from ten or more individuals who are members of the target population. Ideally, the individuals represent typical members of the target population. In a target population of Caucasian ancestry, the samples used to create the reference sample can include both female and male Caucasian individuals.

Next, the reference population sample is constructed by obtaining representative samples of genetic material from members of the target population. The reference population sample can be constructed by obtaining samples of genetic material from individual donors. Ten Caucasian donors are chosen to create the reference population sample. Five of the donors are Caucasian females and five of the donors are Caucasian males.

Samples of genetic material are obtained from each reference donor. The allele frequencies of each SNP are measured in each sample, and the results are recorded. The values obtained for each SNP are summed across all ten of the donor samples and the mean allele frequency value is determined. The mean allele frequency value of each SNP (e.g., a reference SNP signature) can then be used in subsequent analyses as the mean allele frequency value of the reference population.

Example 12

During the investigation of a crime, it can be useful to establish that a particular individual or individuals did not contribute genetic material to a given forensic sample. This can be touching a common surface, such as a door handle, toilet seat, or other common surface. In this example, the methods in the current disclosure are used to verify that genetic material from a given subject is not present in a forensic sample.

First, a sample of genetic material is obtained from a subject. The sample is analyzed and the allele frequencies of the SNPs in the sample are determined (providing a subject SNP signature).

Next, genetic material is isolated from the forensic sample. The sample is analyzed and the allele frequencies of the SNPs in the sample are determined (providing a sample SNP signature).

Once the allele frequencies of the SNPs have been obtained for both the subject and the forensic sample, one compares the two in order to see if there are any SNPs present in the subject SNP signature that are absent from the sample SNP signature. A significant number of absent SNPs will indicate that the subject did not contribute to the forensic sample.

In the alternative, the comparison can also include a reference SNP signature, where the subject's genetic material is also represented in the reference SNP signature, and the comparison can be between a) the subject SNP signature and the reference SNP signature, and b) the subject SNP signature and the sample SNP signature, in order to demonstrate that the subject is more likely to have contributed to the reference population than to the forensic sample.

Example 13

A forensic sample can contain genetic material from one or more unknown individuals. This example demonstrates how the currently disclosed methods can be used to determine whether a complex sample contains genetic material from one or more unknown subjects.

Genetic material from a forensic sample is isolated and characterized to obtain a sample SNP signature.

Genetic material from a subject is isolated and characterized to obtain a subject SNP signature.

Genetic material from a reference sample is isolated and characterized to obtain a reference SNP signature. The subject will be a member of the reference population and thus represented in the reference SNP signature.

The three SNP signatures are compared and the results indicate that the subject is not likely to have contributed to the genetic material in the forensic sample or that, while the subject did contribute to the forensic sample, at least one other subject, with a SNP signature difference from the subject's SNP signature, also contributed to the forensic sample.

Example 14

This example demonstrates one method of determining if any one of a number of subjects contributed to a test genetic material sample.

Genetic material from a forensic sample is isolated and characterized to obtain a sample SNP signature.

Genetic material from 100 subjects is isolated and characterized to obtain a subject SNP signature. The subject SNP signature includes the mean frequencies of the various SNPs across the 100 subjects.

Genetic material from a reference population is isolated and characterized to obtain a reference SNP signature.

The three SNP signatures are compared, as described herein. The results demonstrate that at least one of the 100 subjects contributed to the test genetic material sample. In an alternative arrangement, additional individual comparisons can be made to determine which of the 100 subjects contributed to the test genetic material sample.

Example 15

This Example outlines how one can analyze SNP signatures. One obtains a reference SNP signature, a subject SNP signature, and a sample SNP signature. Each of the signatures includes the intensity levels from SNP microarrays from one of the microarrays of a reference sample, a subject sample, or a test genetic material sample. One then compares two models, one where the individual of interest is assumed to be in the mixture, and another where the individual of interest is assumed not to be in the mixture, in the form of a posterior odds ratio (as explained in the detailed description above). One derives the likelihood of each of the two models using Bayesian inference to accurately assess the probability of the observations (as described in the detailed description above). With this method, a more robust and accurate model of the observations is created, giving a better statistical measure of evidence.

INCORPORATION BY REFERENCE

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls. In addition, "Resolving Individuals Contributing Trace Amounts of DNA to Highly Complex Mixtures Using High-Density SNP Genotyping Microarrays," PLoS Genentics, August 2008, Vol. 4, 8, p. 1-9, is hereby incorporated by reference in its entirety, including any discussion regarding the methods disclosed therein, various applications of those methods, various formulas regarding the methods, and how to define and derive the various components of those formulas.

EQUIVALENTS

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

The use of the words "function," "means" or "step" in the Detailed Description or Description of the Drawings or claims is not intended to indicate a desire to invoke the special provisions of 35 U.S.C. § 112, ¶6, to define the invention. To the contrary, if the provisions of 35 U.S.C. § 112, ¶6 are sought to be invoked to define the inventions, the claims will specifically and expressly state the exact phrases "means for" or "step for, and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then the provisions of 35 U.S.C. § 112, ¶6 are not invoked. Moreover, even if the provisions of 35 U.S.C. § 112, ¶6 are invoked to define the claimed inventions, it is intended that the inventions not be limited only to the specific structure, material or acts that are described in the preferred embodiments, but in addition, include any and all structures, materials or acts that perform the claimed function as described in alternative embodiments or forms of the invention, or that are well known present or later-developed, equivalent structures, material or acts for performing the claimed function.

We claim:

1. A method of analyzing complex forensic samples to identify a statistical probability of the presence of genetic material of a person of interest (POI) in a complex forensic DNA sample, the method comprising the use of at least one special purpose computing device, the method comprising:
    accessing a database storing genomic sequencing information for at least two of a reference population, the POI, and the complex forensic DNA sample, wherein the accessing is executed by a hardware processor;
    identifying a statistical probability of the presence of genetic material of the POI in the complex forensic DNA sample based on genomic analysis of the complex forensic DNA sample, wherein the identifying is executed by the hardware processor, the genomic analysis comprising:
        performing a single nucleotide polymorphism (SNP) analysis on a genetic material sample of the POI to acquire a first allele frequency for a selected SNP of the POI;
        providing a second allele frequency for the selected SNP from the reference population of genetic material, the reference population having ancestrally informative markers matched to the POI and having a reference population SNP signature for a plurality of SNPs;
        measuring a third allele frequency for the selected SNP with a high-throughput SNP genotyping microarray for the complex forensic sample, wherein the complex forensic sample is contaminated with at least one of a bacterial genetic material, a nonhuman genetic material, a human genetic material from a human other than the POI, or a degraded genetic material;
        repeating the above processes for at least 50 different selected SNPs to create a complex forensic sample SNP signature and a POI SNP signature;
        comparing the complex forensic sample SNP signature to the POI SNP signature and the reference population SNP signature by computing a first bias of an allele frequency within SNPs of the complex forensic sample relative to the POI and computing a second bias of an allele frequency within SNPs of the complex forensic sample relative to the reference population to determine the statistical probability of the presence of the genetic material of the POI in the complex forensic sample, wherein the determination of the statistical probability is determined without computationally considering the number of individuals that contributed to the complex forensic sample; and
    outputting, to a computing device having a display, the statistical probability of the presence of the POI's genetic material in the complex forensic sample based on the computed results, thereby identifying the probability of whether the presence of the genetic material of the POI is in the complex forensic sample.

2. The method of claim 1, wherein computing a bias is achieved by the following processes: a) determining the absolute value of the difference in the allele frequencies of the POI and the reference population; b) determining the absolute value of the difference in the allele frequencies of the person of interest and the complex forensic sample; and c) subtracting b) from a) to obtain a distance value for the SNP.

3. The method of claim 2, wherein when the distance value for the SNP is positive, it is more likely that the POI contributed genetic material to the complex forensic sample, when the distance value is negative, the POI'S genetic material is more likely to be part of the reference sample, and when the distance value is 0, the POI'S genetic material is equally likely to be in the complex forensic sample and the reference sample.

4. The method of claim 3, wherein the above processes are repeated for at least 50,000 SNPs.

5. The method of claim 3, wherein the frequencies are expressed as a numerical value.

6. The method of claim 3, wherein the frequencies are expressed as fluorescence levels.

7. The method of claim 3, wherein the frequencies are expressed as normalized values for the POI, reference population, and complex forensic sample.

8. The method of claim 1, wherein computing the bias of allele frequencies within SNPs of the complex forensic sample relative to the reference population and the POI allows one to determine if there is at least a 99% likelihood that the POI contributed to the complex forensic sample.

9. The method of claim 1, wherein computing the bias of allele frequencies within SNPs of the complex forensic sample relative to the reference population and the POI determines that the complex forensic sample contains genetic material from a person other than the POI.

10. The method of claim 1, wherein computing the bias of allele frequencies within SNPs of the complex forensic sample relative to the reference population and the POI determines a likelihood that the complex forensic sample contains genetic material from the person of interest.

11. The method of claim 1, wherein the complex forensic sample comprises degraded genetic material.

12. The method of claim 1, wherein the complex forensic sample is collected from a crime scene and the characterization is performed to identify if the complex test genetic material sample includes DNA from the person of interest.

13. The method of claim 1, further comprising the process of collecting a complex forensic sample, running the sample on a SNP detecting array, and monitoring what SNPs are present in the sample, thereby measuring the third allele frequency for the SNP for the complex forensic sample.

14. The method of claim 1, wherein measuring a third allele frequency for the SNP for the complex forensic sample comprises having the frequency for the SNP for the complex forensic sample.

15. The method of claim 1, wherein the characterization comprises the following analysis:

$$T(Y_i) = (\text{mean}(D(Y_{i,j})) - \mu_0)/(sd(D(Y_{i,j}))/\text{sqrt}(s)))$$

wherein $\mu_0$ is the mean of $D(Y_k)$ over individuals $Y_k$ not in the mixture, $sd(D(Y_{i,j}))$ is the standard deviation of $D(Y_{i,j})$ for all SNPs j and individual $Y_i$, sqrt(s) is the square root of the number of SNPs, and $D(Y_{i,j}) = |Y_{i,j} - Pop_j| - |Y_{i,j} - M_j|$, where $Y_{i,j}$=allele frequency of individual for SNP j, $Pop_j$=allele frequency of reference population for SNP j, and $M_j$=allele frequency of mixture for SNP j.

16. The method of claim 15, wherein $\mu_0$ is zero.

17. The method of claim 1, wherein the complex forensic sample comprises genetic material from at least 10 different organisms.

18. The method of claim 1, wherein the complex forensic sample comprises genetic material from at least two different humans.

19. The method of claim 1, wherein the complex forensic sample comprises genetic material from at least 100 different organisms.

20. The method of claim 1, wherein the determination of the statistical probability is determined without knowing the number of individuals that contributed to the complex forensic sample.

21. The method of claim 1, wherein the method is performed on a computer and wherein the characterization is output to a user.

22. The method of claim 21, wherein the computer comprises software for implementing the method.

23. The method of claim 1, further comprising comparing the complex forensic sample SNP signature to a second reference population SNP signature.

24. A method of analyzing complex forensic samples to identify a statistical probability of the presence of genetic material of a person of interest (POI) in a complex forensic DNA sample, the method comprising the use of at least one special purpose computing device, the method comprising:

accessing a database storing genomic sequencing information for at least two of a reference population, the POI, and the complex forensic DNA sample, wherein the accessing is executed by a hardware processor;

identifying a statistical probability of the presence of genetic material of the POI in the complex forensic DNA sample based on genomic analysis of the complex forensic DNA sample, wherein the identifying is executed by the hardware processor, the genomic analysis comprising:

performing a single nucleotide polymorphism (SNP) analysis on a genetic material sample of the POI to acquire a first allele frequency for a selected SNP of the POI;

providing a second allele frequency for the selected SNP from the reference population of genetic material, the reference population having ancestrally informative markers matched to the POI and having a reference population SNP signature for a plurality of SNPs;

measuring a third allele frequency for the selected SNP with a high-throughput SNP genotyping microarray for the complex forensic sample, wherein the complex forensic sample is contaminated with at least one of a bacterial genetic material, a nonhuman genetic material, a human genetic material from a human other than the POI, or a degraded genetic material;

repeating the above processes for at least 50 different selected SNPs to create a complex forensic sample SNP signature and a POI SNP signature;

storing the POI SNP signature in a first memory location;

storing the reference population SNP signature in a second memory location;

storing the complex forensic sample SNP signature in a third memory location;

identifying whether the POI's genetic material is present in the complex forensic sample by forensically analyzing the complex forensic sample SNP signature compared to the POI SNP signature and the reference population SNP signature by computing a first bias of an allele frequency within SNPs of the complex forensic sample relative to the POI and computing a second bias of an allele frequency within SNPs of the complex forensic sample relative to the reference population to determine the statistical probability of the presence of the genetic material of the POI in the complex forensic sample, wherein the determination of the statistical probability is determined without computationally considering the number of individuals that contributed to the complex forensic sample; and outputting, to a computing device having a display, the statistical probability of the presence of the POI's genetic material in the complex forensic sample based on the computed results, thereby identifying the probability of whether the presence of the genetic material of the POI is in the complex forensic sample.

25. A method of analyzing complex DNA samples to identify a statistical probability of the presence of genetic material of a person of interest (POI) in a complex DNA sample, the method comprising the use of at least one special purpose computing device, the method comprising:

accessing a database storing genomic sequencing information for at least two of a reference population, the POI, and the complex forensic DNA sample, wherein the accessing is executed by a hardware processor;

identifying a statistical probability of the presence of genetic material of the POI in the complex forensic DNA sample based on genomic analysis of the complex forensic DNA sample, wherein the identifying is executed by the hardware processor, the genomic analysis comprising:

performing a single nucleotide polymorphism (SNP) analysis on a genetic material sample of the POI to acquire a first allele frequency for a selected SNP of the POI;

providing a second allele frequency for the selected SNP from the reference population of genetic material, the reference population having ancestrally informative markers matched to the POI and having a reference population SNP signature for a plurality of SNPs;

measuring a third allele frequency for the selected SNP with a high-throughput SNP genotyping microarray for the complex DNA sample, wherein the complex DNA sample is contaminated with at least one of bacterial DNA, nonhuman DNA, or human DNA from a human other than the POI;

repeating the above processes for at least 50 different selected SNPs to create a complex DNA sample SNP signature and a POI SNP signature;

comparing the complex DNA sample SNP signature to the POI SNP signature and the reference population SNP signature by computing a first bias of an allele frequency within SNPs of the complex DNA sample relative to the POI and computing a second bias of an allele frequency within SNPs of the complex DNA sample relative to the reference population to determine the statistical probability of the presence of the genetic material of the POI in the complex DNA sample, wherein the determination of the statistical probability is determined without computationally considering the number of individuals that contributed to the complex DNA sample; and outputting, to a computing device having a display, the statistical probability of the presence of the POI'S genetic material in the complex DNA sample based on the computed results, thereby identifying the probability of whether the presence of the genetic material of the POI is in the complex DNA sample.

* * * * *